US010959735B2

(12) United States Patent
Morsi

(10) Patent No.: US 10,959,735 B2
(45) Date of Patent: Mar. 30, 2021

(54) ADVANCED ENDOVASCULAR CLIP AND METHOD OF USING SAME

(71) Applicant: NOHA, LLC, Houston, TX (US)

(72) Inventor: Hesham Morsi, Houston, TX (US)

(73) Assignee: NOHA, LLC, Houston, TX (US)

(*) Notice: Subject to any disclaimer, the term of this patent is extended or adjusted under 35 U.S.C. 154(b) by 137 days.

(21) Appl. No.: 16/028,143

(22) Filed: Jul. 5, 2018

(65) Prior Publication Data

US 2018/0310942 A1 Nov. 1, 2018

Related U.S. Application Data

(63) Continuation-in-part of application No. 13/154,265, filed on Jun. 6, 2011, now Pat. No. 10,028,745.

(60) Provisional application No. 61/516,175, filed on Mar. 30, 2011.

(51) Int. Cl.
*A61B 17/12* (2006.01)
*A61B 17/00* (2006.01)

(52) U.S. Cl.
CPC .... *A61B 17/12022* (2013.01); *A61B 17/1215* (2013.01); *A61B 17/12031* (2013.01); *A61B 17/12113* (2013.01); *A61B 17/12172* (2013.01); *A61B 17/12177* (2013.01); *A61B 2017/00867* (2013.01); *A61B 2017/00871* (2013.01); *A61B 2017/00893* (2013.01)

(58) Field of Classification Search
CPC ........ A61B 17/12022; A61B 17/12031; A61B 17/12113; A61B 17/1215; A61B 17/12172; A61B 17/12177
See application file for complete search history.

(56) References Cited

U.S. PATENT DOCUMENTS

| 4,311,146 A | 1/1982 | Wonder |
| 4,341,218 A | 7/1982 | Ü |
| 4,360,023 A | 11/1982 | Sugita et al. |
| 4,364,392 A | 12/1982 | Strother et al. |
| 4,395,806 A | 8/1983 | Wonder et al. |
| 4,484,581 A | 11/1984 | Martin et al. |
| 4,658,822 A | 4/1987 | Kees |
| 4,660,558 A | 4/1987 | Kees, Jr. |
| 4,710,192 A | 12/1987 | Liotta et al. |

(Continued)

FOREIGN PATENT DOCUMENTS

| JP | 1249045 A | 10/1989 |
| JP | 2154748 A | 6/1990 |

(Continued)

OTHER PUBLICATIONS

Company News on Call, "NMT Medic. Announces Agreement to Sell Vena Cava Filter Assets", http://www.prnewswire.com, Feb. 15, 2002, p. 1 of 2.

(Continued)

*Primary Examiner* — Robert A Lynch
(74) *Attorney, Agent, or Firm* — Norton Rose Fulbright US LLP

(57) ABSTRACT

Embodiments disclosed herein are directed towards an endovascular clip comprising a proximal anchoring member and a distal self-expanding member. The proximal anchoring member and distal self-expanding member are configured to extend across opposite sides of a neck of an aneurysm.

23 Claims, 27 Drawing Sheets

(56) References Cited

U.S. PATENT DOCUMENTS

| | | | |
|---|---|---|---|
| 4,765,335 A | 8/1988 | Schmidt | |
| 4,932,955 A | 6/1990 | Merz et al. | |
| 4,966,603 A | 10/1990 | Focelle et al. | |
| 5,122,136 A | 6/1992 | Guglielmi et al. | |
| 5,411,549 A | 5/1995 | Peters | |
| 5,423,829 A | 6/1995 | Pham et al. | |
| 5,522,823 A | 6/1996 | Kuntz et al. | |
| 5,522,836 A | 6/1996 | Palmero | |
| 5,540,680 A | 7/1996 | Guglielmi et al. | |
| 5,624,449 A | 4/1997 | Pham et al. | |
| 5,634,932 A | 6/1997 | Schmidt | |
| 5,702,418 A | 12/1997 | Ravenscroft | |
| 5,733,294 A | 3/1998 | Forber et al. | |
| 5,749,894 A | 5/1998 | Engelson | |
| 5,758,420 A | 6/1998 | Schmidt et al. | |
| 5,769,816 A | 6/1998 | Barbut et al. | |
| 5,776,097 A | 7/1998 | Massoud | |
| 5,795,331 A | 8/1998 | Cragg et al. | |
| 5,824,059 A | 10/1998 | Wijay | |
| 5,855,578 A | 1/1999 | Guglielmi et al. | |
| 5,868,783 A | 2/1999 | Tower | |
| 5,891,128 A | 4/1999 | Gia et al. | |
| 5,895,385 A | 4/1999 | Guglielmi et al. | |
| 5,919,187 A | 7/1999 | Guglielmi et al. | |
| 5,921,957 A | 7/1999 | Killion et al. | |
| 5,925,016 A | 7/1999 | Chornenky et al. | |
| 5,925,037 A | 7/1999 | Guglielmi et al. | |
| 5,928,226 A | 7/1999 | Guglielmi et al. | |
| 5,928,260 A | 7/1999 | Chin et al. | |
| 5,935,148 A | 8/1999 | Villar et al. | |
| 5,941,888 A | 8/1999 | Wallace et al. | |
| 5,941,896 A | 8/1999 | Kerr | |
| 5,944,714 A | 8/1999 | Guglielmi et al. | |
| 5,947,962 A | 9/1999 | Guglielmi et al. | |
| 5,947,963 A | 9/1999 | Guglielmi | |
| 5,976,126 A | 11/1999 | Guglielmi | |
| 5,976,162 A | 11/1999 | Doan et al. | |
| 5,984,929 A | 11/1999 | Bashiri et al. | |
| 6,010,498 A | 1/2000 | Guglielmi | |
| 6,015,424 A | 1/2000 | Rosenbluth et al. | |
| 6,017,977 A | 1/2000 | Evans et al. | |
| 6,024,754 A | 2/2000 | Engelson | |
| 6,048,333 A | 4/2000 | Lennox et al. | |
| 6,051,607 A | 4/2000 | Greff | |
| 6,053,941 A | 4/2000 | Lindenberg et al. | |
| 6,059,779 A | 5/2000 | Mills | |
| 6,066,133 A | 5/2000 | Guglielmi et al. | |
| 6,077,260 A | 6/2000 | Wheelock et al. | |
| 6,083,220 A | 7/2000 | Guglielmi et al. | |
| 6,096,021 A | 8/2000 | Helm et al. | |
| 6,123,714 A | 9/2000 | Gia et al. | |
| 6,146,396 A | 11/2000 | Konya et al. | |
| 6,258,115 B1 | 7/2001 | Dubrul | |
| 6,315,787 B1 | 11/2001 | Tsugita et al. | |
| 6,342,064 B1 | 1/2002 | Koike et al. | |
| 6,454,780 B1 | 9/2002 | Wallace | |
| 6,488,706 B1 | 12/2002 | Solymar | |
| 6,585,748 B1 | 7/2003 | Jeffree | |
| 6,855,154 B2 | 2/2005 | Abdel-Gawwad | |
| 6,878,161 B2* | 4/2005 | Lenker | A61F 2/07 623/1.12 |
| 7,195,636 B2 | 3/2007 | Avellanet et al. | |
| 7,367,986 B2 | 5/2008 | Mazzocchi et al. | |
| 7,468,072 B2 | 12/2008 | Morsi | |
| 7,914,549 B2 | 3/2011 | Morsi | |
| 7,993,364 B2 | 8/2011 | Morsi | |
| 8,062,379 B2 | 11/2011 | Morsi | |
| 8,075,585 B2 | 12/2011 | Lee et al. | |
| 8,100,938 B2 | 1/2012 | Figulla et al. | |
| 8,292,914 B2 | 10/2012 | Morsi | |
| 8,313,505 B2 | 11/2012 | Amplatz et al. | |
| 8,372,088 B2 | 2/2013 | Morsi | |
| 9,084,589 B2 | 7/2015 | Moszner | |
| 2001/0012951 A1 | 8/2001 | Bates et al. | |
| 2002/0010481 A1 | 1/2002 | Jayaraman | |
| 2002/0038140 A1 | 3/2002 | Yang et al. | |
| 2003/0028209 A1 | 2/2003 | Teoh et al. | |
| 2003/0028213 A1 | 2/2003 | Thill et al. | |
| 2003/0055455 A1 | 3/2003 | Yang et al. | |
| 2003/0093108 A1* | 5/2003 | Avellanet | A61B 17/12172 606/194 |
| 2003/0195553 A1 | 10/2003 | Wallace et al. | |
| 2005/0043786 A1 | 2/2005 | Chu et al. | |
| 2005/0131443 A1 | 6/2005 | Abdel-Gawwad | |
| 2006/0167494 A1 | 7/2006 | Suddaby | |
| 2006/0282111 A1 | 12/2006 | Morsi | |
| 2007/0106311 A1* | 5/2007 | Wallace | A61B 17/12113 606/151 |
| 2007/0179527 A1* | 8/2007 | Eskuri | A61B 17/0057 606/213 |
| 2008/0200945 A1 | 8/2008 | Amplatz et al. | |
| 2008/0312684 A1 | 12/2008 | Drasler et al. | |
| 2009/0210048 A1 | 8/2009 | Amplatz et al. | |
| 2011/0213407 A1 | 9/2011 | Morsi | |
| 2012/0253369 A1 | 10/2012 | Morsi | |
| 2013/0310803 A1 | 11/2013 | Morsi | |

FOREIGN PATENT DOCUMENTS

| | | |
|---|---|---|
| JP | 3060652 A | 3/1991 |
| JP | 9070405 A | 3/1997 |
| WO | 97/04813 A1 | 2/1997 |
| WO | 97/27888 A1 | 8/1997 |
| WO | 97/45131 A1 | 12/1997 |
| WO | 98/09570 A1 | 3/1998 |

OTHER PUBLICATIONS

International Search Report and Written Opinion in foreign proceedings PCT/US2012/030371, dated Jul. 24, 2012, 19 pages.

IUPAC. Compendium of Chemical Terminology, 2nd ed. (the "Gold Book"). Compiled by A.D. McNaught and A. Wilkinson. Blackwell Scientific Publications, Oxford, 1997.

K.I. Arnautovic, et al., "A Combined Microsurgical Skull-Base and Endovascular Approach to Giant and Large Paraclinoid Aneurysms", Elsevier Science, Inc., 1998, pp. 504-516.

Micrus Corporation, "Micrus Microcoil Delivery System", 2001, Micrus Corporation, http://www.micruscorp.com/coils.html, Feb. 15, 2002, p. 1 of 2.

Mizuho, "Sugita Aneurysm Clips", http://www.mizuho.com/aclips1.html, Feb. 15, 2002, p. 1 of 1.

Office Action from U.S. Appl. No. 12/434,137, dated Dec. 6, 2010, 9 pages.

Onyx™ Liquid Embolic System, http://www.microtherapeutics.com/products_onyx.html, Feb. 15, 2002, p. 1 of 3.

ORCMT, Success Story, "Clinical Neuro Systems", http://orcmt.oakridge.org/success/clinical.html, Feb. 15, 2002, p. 1 of 2.

Puay-Yong Ng, et al., "Intraoperative Endovascular Treatment as an Adjunct to Microsurgical Clipping of Paraclinoid Aneurysms", J. Neurosurg., vol. 93, Oct. 2000, pp. 554-559.

T. Schmitz-Rode, et al., Embolotherapy of Aneurysms Under Temporary Balloon Occlusion of the Neck, Investigative Radiology, 1999, pp. 317-321.

T. Schmitz-Rode, et al., Embolotherapy of Aneurysms Under Temporary Balloon Occlusion of the Neck, Invesigative Radiology, 1999, pp. 317-321.

Untitled Stacked Page, Press Releases, Aug. 2001: MicroVention Raises $12.5 Million in Late-Stage Financing: Minimally Invasive Technology Attracts Several New Medical Device Investors, http://www.microvent.com, Feb. 15, 2002, p. 1 of 2.

Yiu-Wah Fan, et al., "Retrograde Suction Decompression of Paraclinoid Aneurysm—A Revised Technique", Elsevier Science, Inc., 1999, pp. 129-131.

* cited by examiner

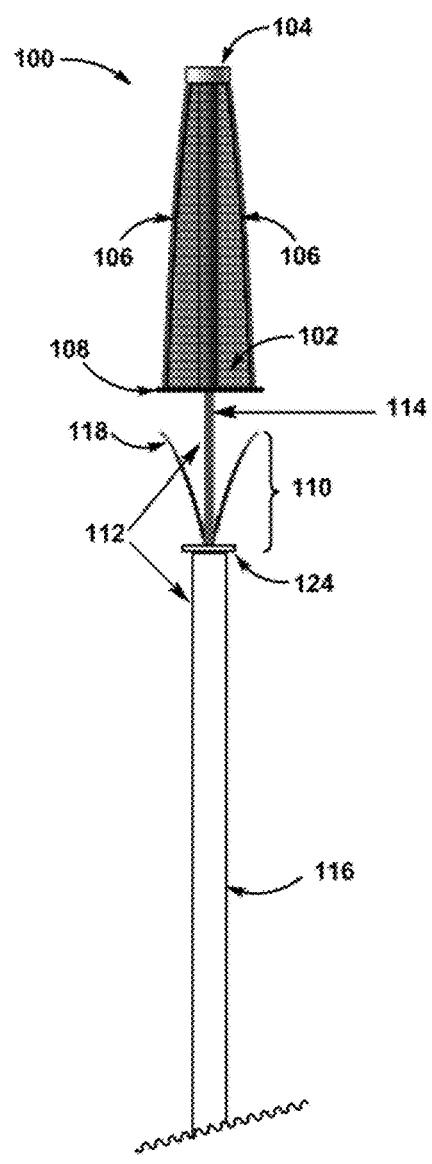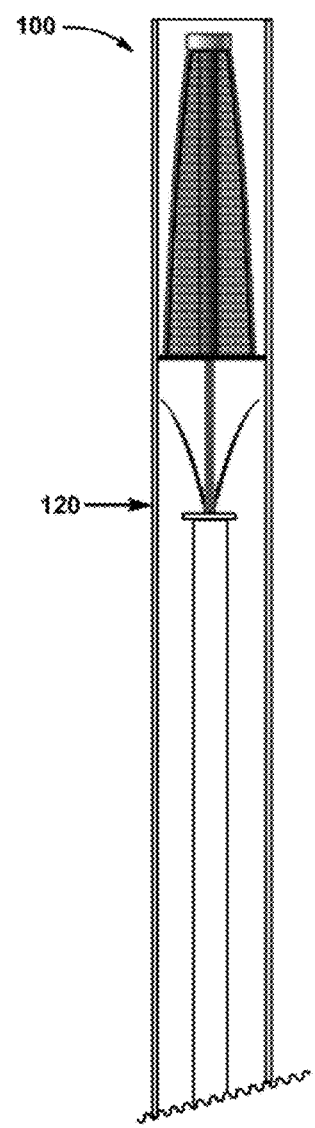
FIGURE 1A
FIGURE 1B

ADVANCED ENDOVASCULAR CLIP AND METHOD OF USING SAME

CROSS-REFERENCE TO RELATED APPLICATIONS

This application is a continuation-in-part application of U.S. patent application Ser. No. 13/154,265 filed Jun. 6, 2011 which is a non-provisional application claiming priority to U.S. Provisional Application No. 61/516,175 filed Mar. 30, 2011, both of which are incorporated herein by reference in their entirety.

FIELD OF THE DISCLOSURE

Embodiments described herein relate generally to medical devices and methods of using same, and more specifically, to medical devices for treating or treating a defect in the vascular wall, such as an aneurysm.

BACKGROUND

Aneurysms result from weakening of the blood vessel, which causes the wall of the blood vessel to balloon outwardly under the hemodynamic stress of the flowing blood, thereby creating an aneurysm. Aneurysm formation and growth can have serious consequences such as pressure on the adjacent brain or other tissues and nerves and eventual rupture which can be fatal.

Given the life-threatening nature of such intracranial aneurysms, several methods of treating aneurysms have been attempted, with varying degrees of success. For example, open craniotomy is a procedure by which an aneurysm is located, and treated extravascularly. This procedure can have significant disadvantages. For example, it is an open surgery in which the surgeon must typically remove a portion of the patient's skull and violate the brain coverings, and can also traumatize brain tissue in order to reach the aneurysm.

Other known techniques used in treating aneurysms are performed endovascularly. Such techniques typically involve attempting to form a mass within the sac of the aneurysm. For instance, a microcatheter is often used to access the aneurysm, where the distal tip of the micro catheter is placed within the sac of the aneurysm, allowing for deposit of embolic material into the sac of the aneurysm. The embolic material includes, for example, detachable coils or liquid polymer. This approach, however, suffers from various disadvantages. For example, the detachable coils can exert pressure on the inside weak walls of the aneurysm, causing ruptures of the aneurysm with a potentially fatal brain hemorrhage. Additionally, coils can migrate out of the sac of the aneurysm and into the parent artery which can lead to clot formation and stroke. Another drawback is that the detachable coils can compact over time due to the space existing between the coils. Coil compaction can result in recanalization of the aneurysm caused by the continued hemodynamic forces from the blood circulation, which is particularly common in bifurcated aneurysms treated with coils.

In addition to the drawbacks associated with coils, embolic liquid migration is also a problem. For instance, when a liquid polymer is injected into the sac of the aneurysm, it can migrate out of the sac of the aneurysm, which can lead to irreversible occlusion of the parent vessel. Techniques have been developed to minimize the risk of coils and embolic liquid migration into the parent vessel, such as temporary occlusion of the parent vessel at the origin of the aneurysm using a removable balloon. However, these techniques suffer from various disadvantages also. For instance, it is sometimes undesirable to occlude the parent vessel, even temporarily. In addition, the migration prevention techniques may not prevent all embolic material migration into the parent vessel, particularly after the removing of the balloon.

Yet another technique to prevent coils migration involves depositing a permanent stent in the parent vessel across the origin of the aneurysm. This technique, however, often require premedicating the patient with strong blood thinner which can be problematic particularly in the setting of ruptured aneurysm and brain hemorrhage.

Another recent trend in endovascular technique for treating cerebral aneurysms involves permanent insertion of a tightly woven high density stent in the parent vessel across the origin of the aneurysm to divert the blood flow away from the aneurysm. This technique also suffers from the disadvantage of needing strong blood thinner, as well as potential inadvertent occlusion of some of the adjacent normal blood vessel, such as perforators. Such occlusion can lead to a devastating stroke. Moreover, the high density stent also suffers from the disadvantage that it cannot be used to treat bifurcated aneurysms.

In view of the above, there remains a need to develop new devices that effectively and safely treat cerebral aneurysms ruptured and unruptured aneurysm.

SUMMARY

The present disclosure provides an endovascular device for treating a defect in the vascular wall such as aneurysm by deploying a self-expandable barrier around the aneurysm neck to block the blood flow to the aneurysm. The present disclosure also provides methods for implementing the endovascular device.

Embodiments described within are directed towards a highly controllable, minimally invasive endovascular clip device for the endovascular treatment of vascular defects. In some embodiments, the device treats bifurcation cerebral aneurysms by providing a deformable disc of mesh to act as a physical barrier delivered to the opening of the defect at the opposite side of normal flowing blood and vessel lumen. The device also supports chronic healing and repairing of the defect and weakness of the vascular wall by providing a tightly adherent focal scaffolding to facilitate the growth of endothelium over the surface of the scaffold and across the defect.

In some embodiments, the endovascular clip device is anchored around the vascular defect by a proximal anchoring member comprising anchoring components and a distal member comprising at least one mesh layer. The proximal and distal members are independently controllable and can be independently manipulated to match the anatomy. Independent control of the proximal and distal members comprises independent translational movement, independent shape adjustment, and independent detachability. The proximal and distal members can lock against opposite sides of a vascular defect. The locked endovascular clip device is held in the desired place by tight adherence to the inside surface of the defect and adjacent vascular wall. The proximal anchoring member comprises a relatively open structure that does not significantly compromise the lumen or impede flow of the parent blood vessels or its branches. In some embodiments, the acute occlusion effect can be further aided by the incorporation of other occlusive elements such as swellable gel. The chronic healing effect can be aided by the incorporation of other growth stimulating elements such as growth factors or patient own vascular stromal stem cells delivered accurately to the site of the defects.

Some embodiments are directed towards an endovascular clip comprising a proximal anchoring member and a distal self-expanding member, wherein the proximal anchoring member and distal self-expanding member are configured to extend across opposite sides of a neck of an aneurysm in their original configurations. In some embodiments, the proximal anchoring member comprises at least two anchoring components. In further embodiments, the distal self-expanding member comprises a mesh or a lattice comprising a plurality of strands intersecting one another, wherein said intersecting strands form a plurality of interstices. In some aspects, the endovascular clip proximal and distal self-expanding members comprise self-expanding material configured to have an original configuration and a deformed configuration. The self-expanding material may be configured to change from said deformed configuration to said original configuration at least by exposure to an activating condition.

In some aspects, the endovascular clip further comprises a concentric delivery system coupled to the proximal anchoring member and the distal self-expanding member. The concentric delivery system comprises a distal detachable wire and a proximal detachable hypotube. Each of the distal detachable wire and a proximal detachable hypotube are independently detachable. In some embodiments, the distal detachable wire and a proximal detachable hypotube are detached in unison. In some aspects, the distal detachable wire and a proximal detachable hypotube comprise additional wires or controlling elements for adjusting different properties of the distal self-expanding member and proximal anchoring member, respectively.

The concentrically-arranged distal detachable wire and a proximal detachable hypotube allow each of the proximal and distal self-expanding members to be separately moved fore and aft, and separately rotated. In some embodiments, the distal detachable wire further comprises a detaching joint detachably coupling distal and proximal portions of the distal detachable wire. Each of the distal detachable wire and a proximal detachable hypotube may be independently detached from the component, e.g., distal and proximal anchoring members, to which it is attached. In some embodiments, the proximal or distal self-expanding member is released from the proximal detachable hypotube or distal detachable wire by rebound of a spring ledge, or other mechanical, chemical, electrolytic, temperature-sensitive, remotely-triggered, or other release mechanism known in the art. In some aspects, the distal detachable wire comprises a locking mechanism that locks the proximal and distal self-expanding members to each other. Locking mechanisms may include a spring ledge lock, ball and glove lock, a pits and leges mechanism, or other locking mechanisms known in the art.

In some embodiments, the distal detachable wire comprises a manually-adjustable steering joint. In some aspects, the proximal anchoring member comprises a proximal detachment zone. In some embodiments, passage of the proximal anchoring member over the locking mechanism activates the locking mechanism. In some embodiments, passage of the proximal anchoring member over the detaching joint activates the detaching joint. In some embodiments, the distal self-expanding member may further comprise a conical shape that, upon deforming, opens in a manner similar to an umbrella.

In some embodiments, the proximal anchoring member comprises at least two anchoring components. A non-limiting list of anchoring component shapes includes loops, lines, curved, oblong, circular, and oval shapes. In a preferred embodiment, the anchoring components point away from a central axis. In some embodiments, the anchoring components may be further attached to rings deployed in the lumen for further anchoring.

In some embodiments, the distal self-expanding member may comprise at least one reinforcing wire. In further embodiments, the distal self-expanding member may comprise at least one peripheral frame. The distal self-expanding member may comprise both one of at least one reinforcing wire and a peripheral frame, both a peripheral frame and at least one reinforcing wire, or neither.

In some embodiments, the endovascular clip comprises a radio-opaque material. The radio-opaque material may be incorporated into any or multiple components of the endovascular clip. The endovascular clip may employ nitinol as the self-expanding material, or any other self-expanding material known to those of skill in the art. In some embodiments, the activating conditions may comprise a temperature above a defined threshold. In other embodiments, the activating conditions comprise a mechanical activation. In some embodiments, the distal self-expanding member lattice comprises a swellable material configured to expand in volume upon exposure to an activating condition. The swellable material may be selected from the group consisting of hydrogel, hydrogel foam, hydrophilic polymers with conjugated collagen, hydrophilic polymers without conjugated collagen, porous hydrated polyvinyl alcohol foam (PAF) gel, and any combination thereof. In some embodiments, the swellable material seals at least a portion of said interstices of the respective deformable component when exposed to the content of the aneurysm. In some embodiments, the distal self-expanding member lattice further comprises a bioactive material configured to promote cell growth. The bioactive material may be a thrombogenic material selected from the group consisting of collagen, fibrinogen, vitronectin, other plasma proteins, growth factors, peptides of said growth factors having attached RGD (arginine glycine-aspartic acid) residues, phospholipids, polymers with phosphorylcholine functionality, and any combination thereof.

The foregoing has outlined rather broadly the features and technical advantages of the embodiments of the present disclosure in order that the detailed description of these embodiments that follows may be better understood. Additional features and advantages of the embodiments of the present disclosure will be described hereinafter which form the subject of the claims of the present disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the present disclosure as set forth in the appended claims. The novel features which are believed to be characteristic of the present disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The following drawings illustrate by way of example and not limitation. For the sake of brevity and clarity, every feature of a given structure may not be labeled in every figure in which that structure appears.

FIGS. 1A-1B are side views of the endovascular clip. FIG. 1B illustrates endovascular clip contained within a catheter.

FIG. 9A is a side view of the preferred embodiment of the present disclosure in a collapsed state being inserted into an aneurysm. FIG. 9B is a side view of the preferred embodiment of the present disclosure with the distal self-expanding member deployed from the catheter lumen into its original, uncompressed state within an aneurysm. FIG. 9C depicts the deformation of the distal self-expanding member mesh as the distal detachable wire is pulled. The distal self-expanding member mesh flattens out against the aneurysm neck and the mesh exerts a restorative force against the aneurysm neck. FIG. 9D depicts the proximal anchoring member exiting from the catheter. FIG. 9E depicts the proximal anchoring member fully outside of the catheter lumen. The anchoring components have opened to their original uncompressed state. FIG. 9F illustrates the anchoring components pressing against the vessel wall/exterior aneurysm neck. As the proximal detachable tube pushes the proximal anchoring member against the aneurysm neck, the anchoring components deform to a more flattened shape. The anchoring components exert a restorative force against the aneurysm neck. The proximal detachment zone has cleared the locking edges, thereby initiating detachment of the proximal anchoring member from the proximal detachable hypotube. FIG. 9G depicts the endovascular clip in place. The proximal detachable hypotube has become detached from the proximal anchoring member. The proximal locking member and the distal self-expanding member are locked in place. The deformed anchoring components and the deformed distal self-expanding member mesh exert restorative forces against the aneurysm neck, thereby providing a tight seal between the endovascular clip and both sides of the aneurysm neck.

DETAILED DESCRIPTION

Figure 2:
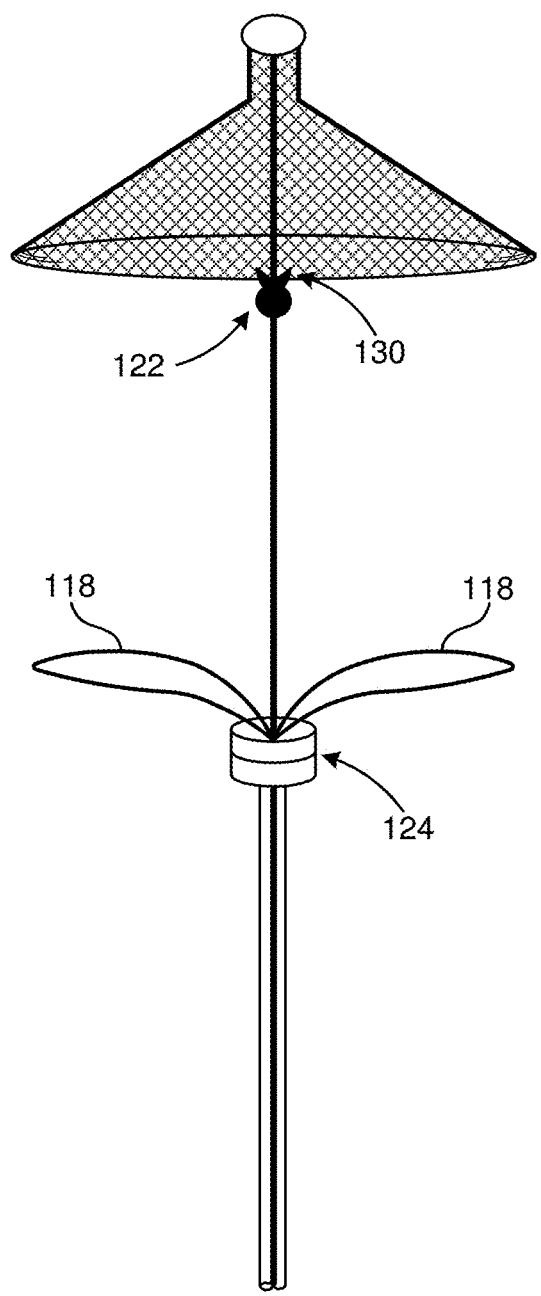
FIG. 2 depicts a preferred embodiment of the endovascular clip with distal self-expanding member and proximal anchoring member in original uncompressed states. Proximal anchoring member comprises a pair of looped anchoring members coupled to the proximal detachment zone. A steering/detachment joint and locking edges are incorporated with distal detachable wire.

The present disclosure provides endovascular therapeutic device and methods for delivering and deploying such devices an within the vasculature of a patient to occlude aneurysms, such as cerebral aneurysms.

Referring to FIG. 1, the endovascular clip 100 comprises aneurysm occluding components distal self-expanding member 102 and proximal anchoring member 110. In a preferred embodiment, the distal self-expanding member 102 comprises a distal disc comprising a mesh or a layer of intersecting wires or strands forming a deformable mesh having a plurality of interstices. The distal self-expanding member 102 and proximal anchoring member 110 are coupled to a concentric delivery system 112. The concentric delivery system 112 comprises an inner distal detachable wire 114 and a proximal detachable hypotube 116. In a preferred embodiment, distal detachable wire 114 is coupled to the distal self-expanding member 102, and proximal detachable hypotube 116 is coupled to proximal anchoring member 110. In some embodiments, each of the distal detachable wire and proximal detachable hypotube is independently controllable. In some aspects, In a preferred embodiment, detachment of the distal detachable wire and proximal detachable hypotube occur in unison. In some embodiments, each of the distal detachable wire and proximal detachable hypotube is independently detachable. That is, detachment of distal detachable wire 114 from distal self-expanding member 102 is independent of detachment of proximal detachable hypotube 116 from proximal anchoring member 110. Detachment of a delivery wire from the self-expanding member to which it is coupled may occur in either order. That is, distal detachable wire 114 may be detached from distal self-expanding member 102 before proximal detachable hypotube 116 is detached from proximal anchoring member 110, or vice versa. In some embodiments, distal detachable wire 114 and/or proximal detachable hypotube 116 comprise additional independently controllable wires to adjust variable components of distal self-expanding member 102 and proximal anchoring member 110.

The distal self-expanding member 102 may be joined to a connecting joint 104, which may act as a central hub for the self-expanding member 102 wire mesh. The connecting joint 104 may serve as a central pivot ring, around which the distal self-expanding member distal disc mesh may be angled upwards and downward. In some embodiments, the distal self-expanding member 102 comprising the distal disc mesh and the one or more distal detachable wires to which it is coupled function in a manner comparable to an umbrella. When the distal self-expanding member 102 moves from a deformed collapsed state to an open undeformed state, the distal disc mesh opens in a distal direction thereby increasing the exposed disc mesh surface area. As depicted in FIG. 1, the collapsed distal self-expanding member 102 distal disc mesh is preferably conically shaped, with the smaller area configured to point in the direction of the aneurysm. This configuration may facilitate the positioning of the distal self-expanding member 102 within the aneurysm. The conical shape of the distal disc mesh aids in anchoring of the distal self-expanding member 102 and the endovascular clip 100.

The preferred original shape of the distal self-expanding member 102 distal disc mesh is a conical shape. After insertion of the distal end of catheter 120 into an aneurysm, the catheter 120 and concentric delivery system 112 are manipulated to allow the distal self-expanding member 102 to exit the catheter 120 and expand from its deformed shape in the catheter to its original, un-compressed state. The distal detachable wire 114 coupled to the distal self-expanding member 102 may then be manipulated to allow the distal self-expanding member distal disc mesh to come into contact with the aneurysm neck. After the distal disc mesh has come into contact with the aneurysm neck, the distal detachable wire 114 may be pulled, thereby flattening the distal disc mesh against the aneurysm neck such that the cone angle increases. As the distal self-expanding member distal disc mesh is forced away from its preferred original shape, the distal disc mesh exerts a restorative force. In some embodiments, this restorative force is provided by memory metal attempting to return the distal disc mesh to its original shape. As the inner delivery wire is pulled further, the distal disc mesh is further displaced from its original shape, thereby increasing the restorative force, which may be transmitted to the aneurysm neck. This restorative force pushes against the aneurysm neck and increases the sealing force of the endovascular clip.

Figure 9A:
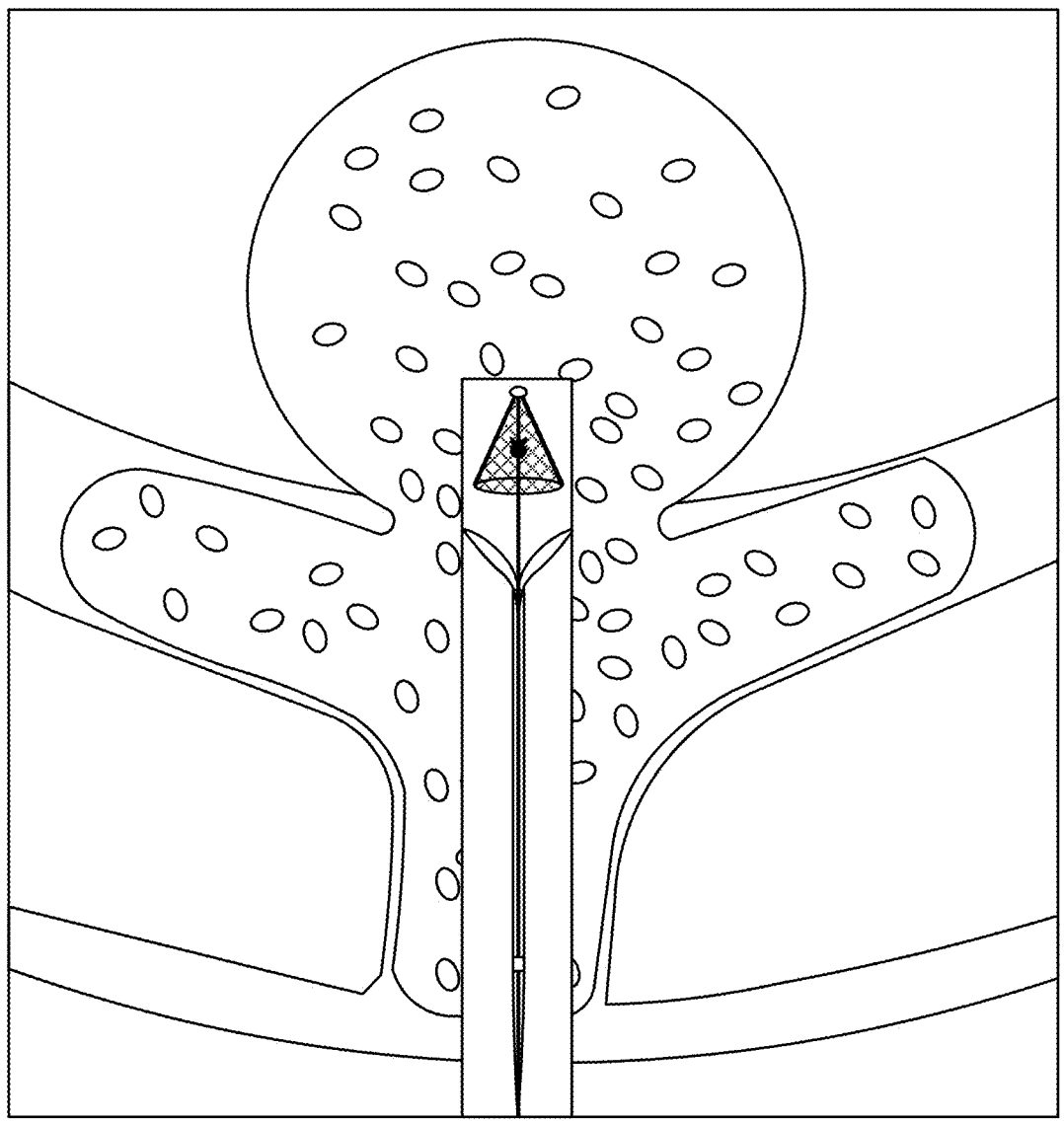
FIGS. 9A-9G depict a process for sealing an aneurysm using one embodiment of the presently claimed apparatus.

The proximal anchoring member 110 comprises two or more anchoring components 118 that work in conjunction with distal self-expanding member 102 to occlude or seal an aneurysm. Referring to FIGS. 1B and 9A, while contained within catheter 114, the proximal anchoring member 110 anchoring components 118 are constrained against the inner catheter walls. Referring to FIG. 1C, when the proximal anchoring member 110 is manipulated out of the catheter, the anchoring components 118 angle away from delivery wire 112, thereby increasing the end-to-end distance of the proximal controllable anchoring member 110. In a preferred embodiment, the anchoring components 118 are looped wires, as depicted in FIG. 1. The anchoring components may comprise other shapes, including looped and non-looped configurations, straight wires, curved wires, oval shapes, circular shapes, oblong shapes, and the like. In a preferred embodiment, two radially-opposed anchoring components are coupled to the proximal anchoring member 110, however more than two anchoring components may be coupled to the proximal anchoring member 110. In some embodiments, the angle between an anchoring component and proximal detachable hypotube 116 is 90° or less. In some embodiments, anchoring components 118 are adjustable such that the angle may be manually adjusted. In some embodiments, the anchoring components 118 are self-expanding. In some aspects, anchoring components 118 are made of memory metal such that the components self-expand to an original uncompressed configuration. In some embodiments, the size and angle of the anchoring components 118 are selected such that the distance between anchoring component free ends is larger than the diameter of the aneurysm neck. In one embodiment, the endovascular clip 100 is anchored at the desired location between proximal anchoring member 110 and the distal self-expanding member 102.

In some embodiments, the proximal anchoring member 110 and distal self-expanding member 102 are separately manipulated to match the anatomy and lock against opposite sides of the vascular defect. This allows for at least the edge of distal self-expanding member 102 and proximal anchoring member 110 to squeeze and attach to the neck of the aneurysm.

The distal self-expanding member 102 distal disc mesh may comprise a superelastic and/or self-expanding material. In particular, superelastic and/or self-expanding material should have properties that allow it to have a deformed shape under one condition and to recover its original shape prior to deformation upon exposure to an activation mechanism. In some embodiments, the material may include a memory-shaped heated alloy such as nitinol, or nickel titanium, which is a metal alloy of nickel and titanium. Nitinol alloys exhibit two closely related and unique properties: shape memory and superelasticity. Shape memory refers to the ability of nitinol to undergo deformation at one temperature, then recover its original, un-deformed shape upon heating above its "transformation temperature." That is, nitinol alloy has a biased self-expanded condition and may be compressed into a collapsed or deformed condition before use. During use, it may be exposed to temperature above the transformation threshold, thereby causing it to revert back to its un-deformed shape.

In certain embodiments, distal self-expanding member 102 may comprise any desired material or combination of materials, including, but not limited to, a metal, an alloy, a composite, a polymer, and the like. For example, the distal disc mesh may comprise nitinol, stainless steel, cobalt chromium, platinum, titanium, plastic, or any combination thereof. The mesh strands may each have a diameter preferably between about 5-200 microns, and more preferably between 40 to 60 microns. In other embodiments, the diameter of the strands are configured to according to the selected size of the endovascular clip 100.

In another embodiment, distal self-expanding member 102 can comprise more than one layer of mesh. The pattern of the mesh may be regular or irregular, as long as the pattern of the strands of the mesh form a plurality of interstices. For instance, the strands of the mesh may be perpendicular to one another such that squares or rectangular openings are formed. In other embodiments, circular or irregularly shaped openings may be formed. In one embodiment, the square or rectangular openings may be of uniform dimensions or they may be of different dimensions. Additional aspects of the density of the strands of the mesh are further discussed below. Preferably, the number and placement of the strands are configured to provide a mesh with a minimum amount of material that is still sufficient to allow the endovascular clip 100 to serve at least as a physical barrier to isolate the aneurysm from the flow of the parent artery. A self-expanding disc with a minimal yet sufficient mesh provides a lighter endovascular clip that allows for better maneuverability when it is being inserted and placed in the patient.

The mesh can be reinforced by a ring or frame 108 that is attached to the distal self-expanding member 102. The frame may be attached to the periphery of distal self-expanding member 102, or anywhere along the distal disc mesh. The frame 108 may comprise a superelastic and/or self-expanding material, such as nitinol, or any other material that provides similar superelasticity properties. In some embodiments, the peripheral frame 108 has a deformed or compressed shape with a smaller diameter than the un-deformed, original shape diameter. The frame 108 may comprise a single strand that has a larger diameter than the strands of the mesh. In one embodiment, the diameter of the frame 108 is at least double the diameter of the strands of the mesh of distal self-expanding member 102. In another embodiment, the diameter of frame 108 is between about 10-500 microns. More preferably, the diameter of the frame 108 is about 80-120 microns The frame 108 can have different un-deformed shapes such as circular, oval, rectangular or any other regular or irregular shapes that may be suitable to the application, e.g., appropriate fit with the neck of a particular aneurysm.

Figure 5:
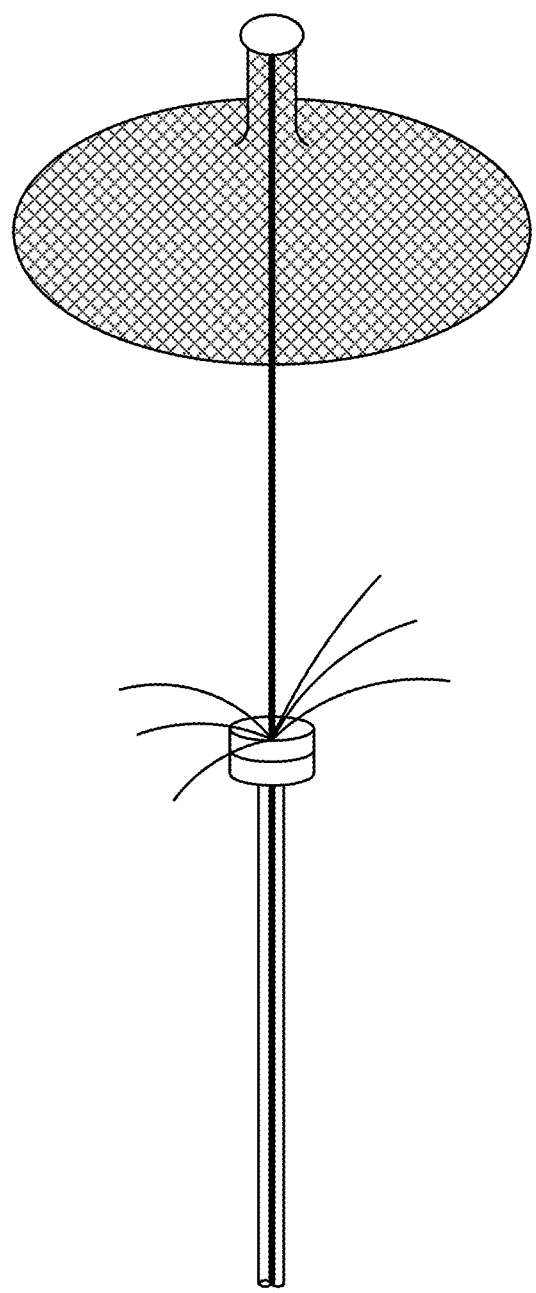
FIG. 5 is an image of one embodiment of the endovascular clip. The distal self-expanding member mesh is conically shaped and does not include a reinforcing wire or a peripheral frame. The distal self-expanding member is fixedly coupled to distal detachable wire. That is, the distal detachable wire does not include a steering joint. The proximal anchoring member comprises six curved, non-looped anchoring members.
Figure 6:
FIG. 6 is an illustration of a distal self-expanding member with a conically-shaped mesh. The distal detachable wire comprises a steering/detachable joint and a pair of locking edges. The steering joint has not been activated such that the distal and proximal portions of the distal detachable wire lie along the same line.
Figure 7:
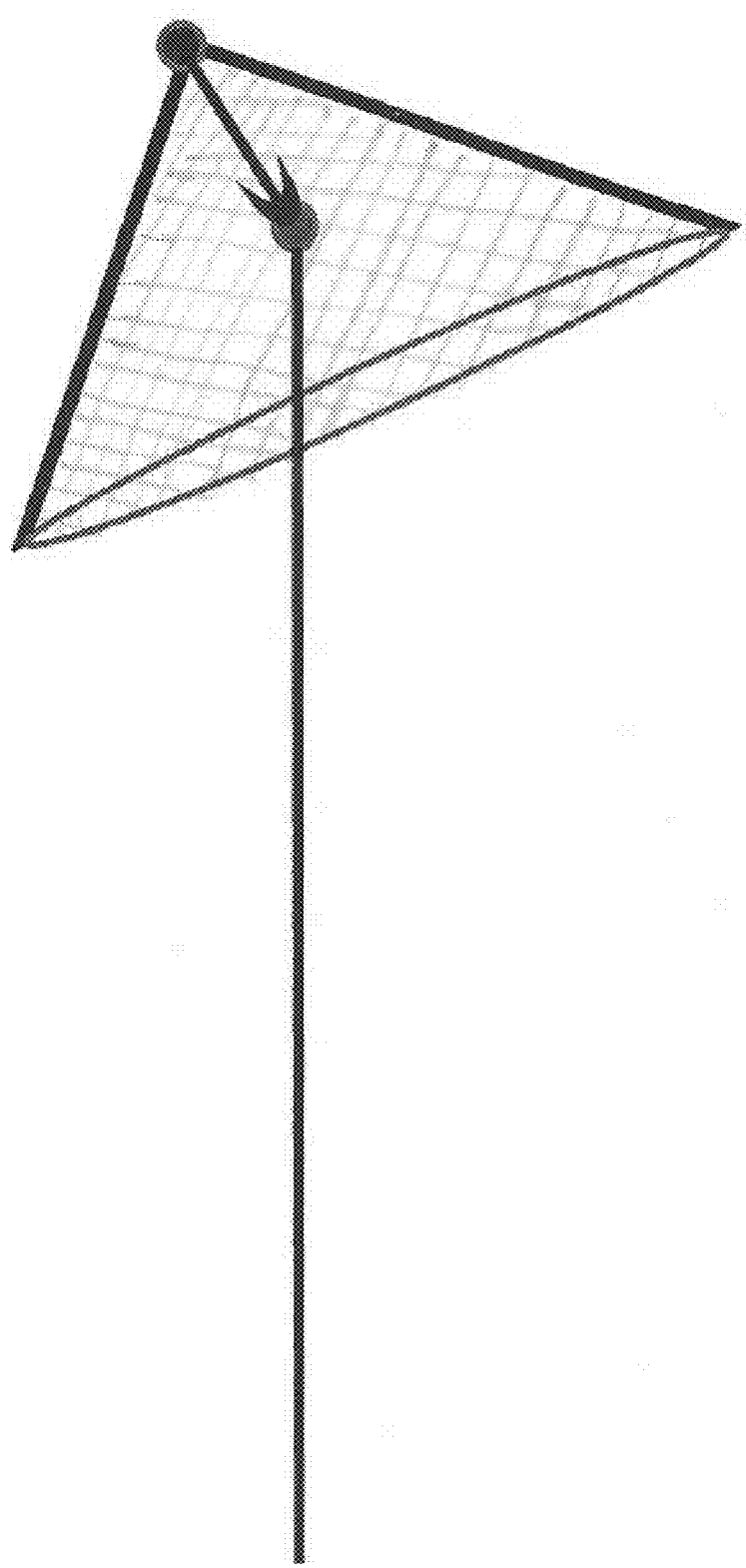
FIG. 7 is an illustration of a distal self-expanding member coupled to a distal detachable with a steering joint that has been angled, or steered away from the distal detachable wire center line.

FIG. 5 shows both distal and proximal members of the endovascular clip 100 in original, uncompressed configuration. FIG. 1B shows both distal and proximal members of the endovascular clip 100 in deformed configurations within the catheter lumen. In some embodiments, the deformed configuration of the distal self-expanding member 102 is generally perpendicular to the original configuration of the distal self-expanding member 102. In a preferred embodiment, the original configuration of the distal self-expanding member 102 is conical in shape.

Referring to FIG. 1, the distal self-expanding member 102 may be coupled to a connecting joint 104. The connecting joint 104 can be made of any desired material or combination of materials, including, but not limited to, a metal, an alloy, a composite, a polymer, and the like. In one embodiment, the connecting joint 104 may be formed from the same material, e.g., nitinol, as that of the distal self-expanding member 102, such that a portion of the mesh and/or reinforcing wire 106 (discussed further below), is integral with a portion of the connecting joint 104. Alternatively, the distal self-expanding member 102 may be welded to the connecting joint 104. In other embodiments, the distal self-expanding member 102 may be attached to connecting joint 104 through appropriate means. In some embodiments, the connecting joint 104 comprises a radiopaque material. Due to the superelastic properties of the mesh of distal self-expanding member 102, the integrity of the material attachment sites between the distal self-expanding member 102 and the connecting joint 104 are preferably minimally affected by the folding and unfolding of the distal self-expanding member 102 during transition between the original and deformed conditions.

In one embodiment, the connecting joint 104 has a diameter between about 0.1-2 mm. In some embodiments, the diameter of the connecting joint 104 is larger than the diameter of the distal detachable wire 114. The distal detachable wire 114 may be attached to the proximal surface of the connecting joint 104 by various means known to those skilled in the art that allow the user to selectively release the connecting joint 104 from distal detachable wire 114. For example, suitable release mechanisms may include mechanical, chemical, electrolytic, temperature-sensitive, remotely-triggered, or other type of release means. One exemplary mechanical release mechanism is a ball mount.

In some embodiments, the mesh of the self-expanding member 102 can further be reinforced by one or more reinforcing wires 106. Referring to FIGS. 1A and 1B, reinforcing wires 106 are preferably connected to opposite sides of peripheral frame 108. As depicted in FIGS. 1A and 1B, a central portion of the reinforcing wire 106 is attached to the connecting joint 104. In some embodiments, at least a portion of the length of the reinforcing wire 106 is attached to the surface of distal disc mesh. In some embodiments, the entire length of reinforcing wire 106 is attached to distal disc mesh. In other embodiments, certain strands of the distal disc mesh are attached to reinforcing wire 106. The reinforcing wire 106 may also made of superelastic and/or self-expanding material, such as memory-shaped heated alloy, e.g., nitinol. As discussed above, the reinforcing wire 106 may be formed from the same material as that of the self-expanding member 102 and connecting joint 104 such that at least a portion of each of these components may be integral with one another. In one embodiment, the reinforcing wire 106 may have a larger diameter than the strands of the mesh. Preferably, the diameter of the reinforcing wire 106 is between about 10-500 microns, and more preferably a diameter of about 50-75 microns. In another embodiment, self-expanding member 102 includes at least one reinforcing wire 106. In embodiments where self-expanding member 102 includes more than one reinforcing wire 106, the wires may be placed to evenly divide the surface of the respective self-expanding disc. For instance, if there are two reinforcing wires 106, they may be placed perpendicular to one another with the intersection being at or near connecting joint 104. Reinforcing wires may be of any shape, including, but not limited to straight wires, loops, veins, and curved shapes. In some embodiments, the distal self-expanding member 102 need not include frame 108. In some embodiments, the distal self-expanding member 102 need not include reinforcing wires 106.

Referring to FIG. 1B, when the clip 100 is in its compressed or deformed state, it is constrained inside the delivery catheter 120. In embodiments having at least one reinforcing wire 106 for distal self-expanding member 102, the reinforcing wire 106 is folded up in a generally longitudinal fashion proximate to the catheter shaft. In embodiments including a reinforcing wire, once the distal self-expanding member 102 of clip 100 is deployed out of the distal end of the catheter 120, the reinforcing wire 106 and the mesh move into their biased or original alignment, thereby bringing the mesh (and the peripheral frame 108, if present) of the distal self-expanding member 102, into the original, uncompressed configuration.

Alternatively, in an embodiment without reinforcing wire 106, this biased alignment can be otherwise achieved without the need for a central reinforcing wire 106. For instance, in one embodiment, a biased or unconstrained horizontal alignment of the distal self-expanding member 102 can be achieved by having some strands of the mesh that are slightly thicker to impart additional strength to the self-expanding member. The thicker wires impart greater strength without significantly increasing the delivery profile of clip 100 while the thinner wires offer support while providing the desired strand density for the mesh and without requiring additional material or increasing the delivery profile. In other embodiments, the mesh may comprise uniform-diameter strands and still be capable of transpositioning itself from a deformed state to an undeformed state in the absence of a reinforcing wire. Various permutations are available where in some embodiments, distal self-expanding member 102 can be configured without a frame 108 and/or reinforcing wire 106. The different thickness or density arrangements of the distal self-expanding member 102 mesh can be adjusted to optimize the member's recovery to any pre-determined position.

The distal self-expanding member 102 and proximal anchoring member 110 are configured with desired deployment characteristics and configured to provide sufficient flexibility for tracking through a possibly tortuous vascular system of an individual, such as the intracranial vascular system. The distal detachable wire 114 may comprise a detachment joint that acts as a separation point between distal and proximal portions of the distal detachable wire 114. In order to improve maneuverability, distal detachable wire 114 may comprise a steering joint at which the distal detachable wire 114 may angle. In some embodiments, the steering joint coincides with a detachment point of distal detachable wire 114. In other embodiments, the steering joint is physically separated from the detaching joint. Various detaching means known to those skilled in the art may be employed, including mechanical, chemical, electrolytic, temperature-sensitive, remotely-triggered, or other type of release means. In some embodiments, this steering/detaching joint 122 divides distal detachable wire 114 into proximal and distal portions. The steering/detaching joint 122 allows the distal end of distal detachable wire 114 to slant or angle away from the proximal end of distal detachable wire 114, with the steering/detaching joint 122 being the angle vertex. The detaching joint portion of steering/detaching joint 122 serves as a disconnection point at which distal self-expanding member 102 may detach from the proximal portion of distal detachable wire 114. In some embodiments, the angle about the steering/detaching joint 122 is controllable such that distal self-expanding member 102 can be turned, aimed, or pointed in a particular direction. This angling about steering/detaching joint 122 improve maneuverability of the distal self-expanding member 102 and increases the delivery precision and sealing effectiveness of endovascular clip 100 is positioned within, and seals an aneurysm. Endovascular clip 100 may be inserted into a blood vessel in any suitable manner, such as through the use of endovascular, percutaneous, or other minimally invasive surgical techniques.

In some embodiments, distal detachable wire 114 is uninterrupted and does not comprise a steering joint. In other embodiments, distal detachable wire 114 comprises a steering joint. In a preferred embodiment, both the steering joint and detaching joint are integrated as steering/detaching joint 122. In other embodiments detaching joint and steering joint are positioned at different points along distal detachable wire 114. In some embodiments, the steering joint is controllable such that the angle of the distal portion of the distal detachable wire 114 is controllable. In some embodiments, distal detachable wire 114 may comprise additional wires or other components known in the art that may be used to control the angle about the steering joint 114. In some embodiments, distal detachable wire 114 comprises a fixed detaching joint and no steering joint such that the angle of the distal detachable wire 114 about the detaching joint is not adjustable.

Figure 9B:
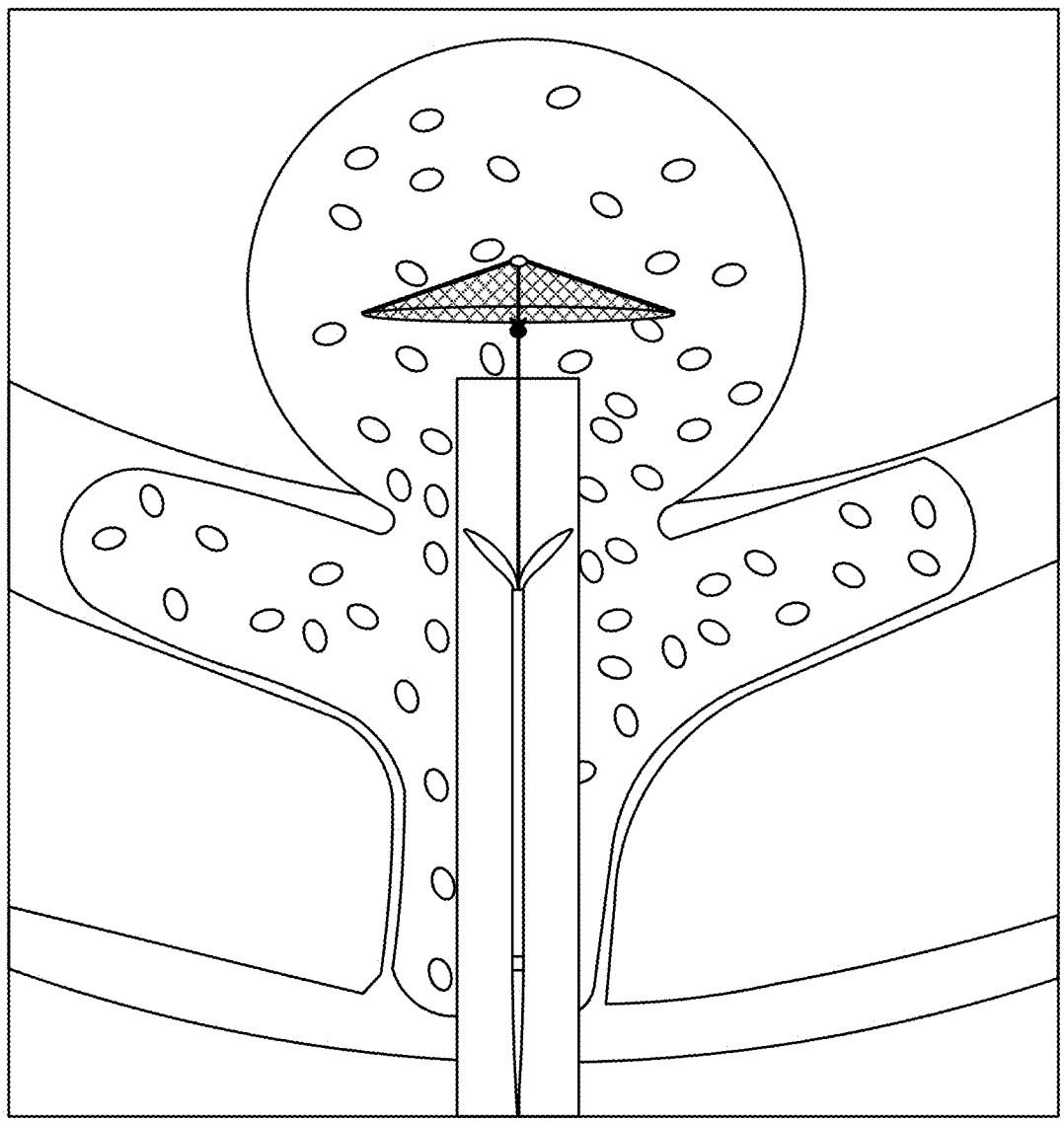
Figure 9C:
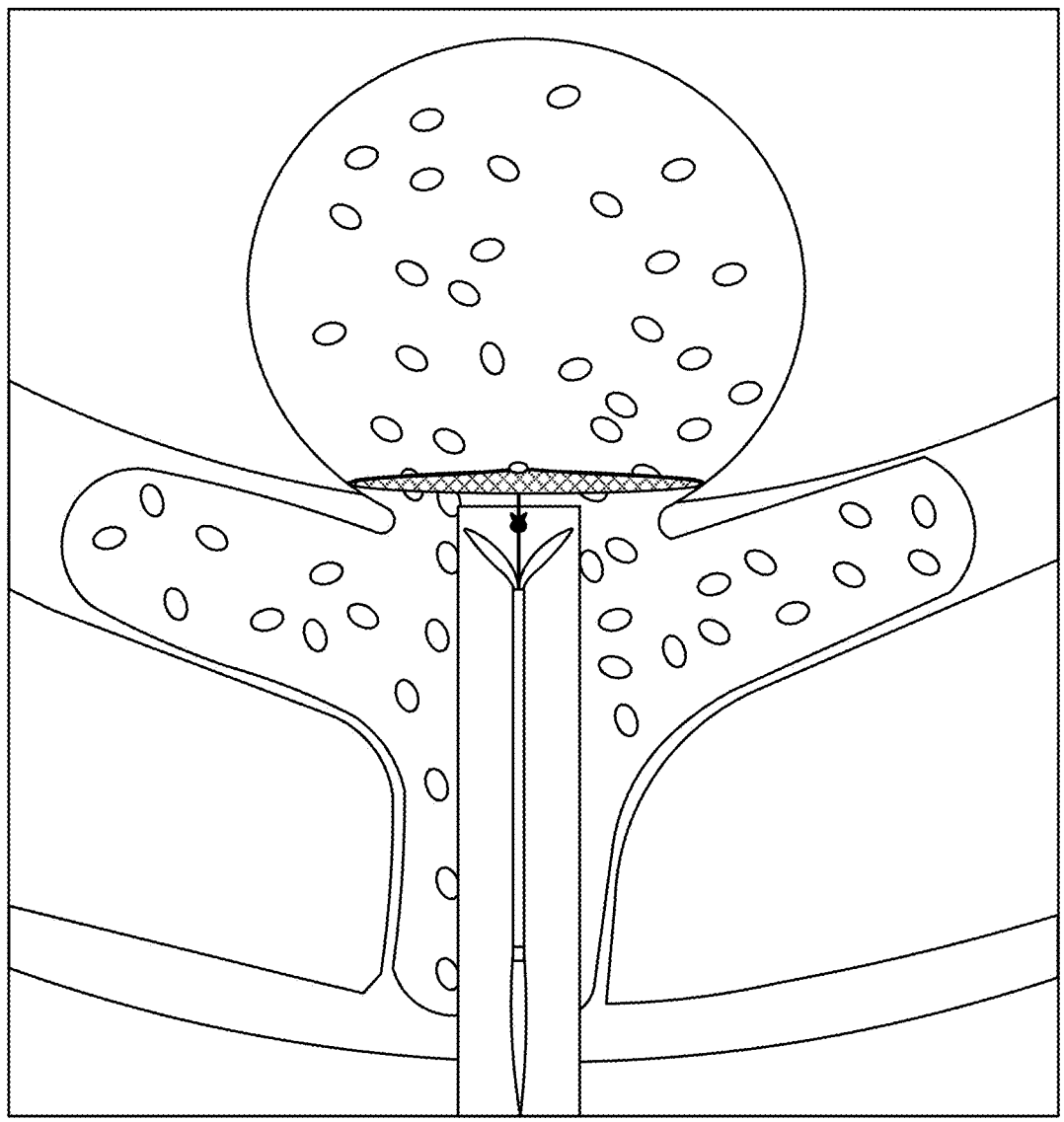

In some embodiments, the detaching joint further comprises a locking means to lockably fix distal self-expanding member 102 and proximal anchoring member 110. In some embodiments, the locking means is activated after a proximal anchoring member detachment zone 124 passes over a lock. In some embodiments distal detachable wire 114 comprises locking ledges 130, which protrude from distal detachable wire 114. In preferred embodiments, the locking ledges 130 are made of memory metal. In some embodiments, the inner diameter of the proximal detachment zone 124 is smaller than the end-to-end distance of locking ledges 130. When the proximal detachment zone 124 passes over locking ledges 130, the locking ledges are pushed inward. As the proximal detachment zone 124 moves past locking ledges 130, the locking ledges revert to their original positions, thereby locking proximal detachment zone 124 against locking ledges 130. In some embodiments a spring or series of spring is employed as a locking mechanism. In other embodiments, other mechanisms for locking one surface against or inside another surface may be employed, including but not limited to piston locks, liner locks, groove locks, cam locks, or a lockback mechanism. As depicted in FIGS. 9F-9G, in some embodiments, locking of proximal detachment zone 124 disrupts connection between proximal anchoring member 110 and proximal detachable hypotube 116. In a preferred embodiment, locking of proximal detachment zone 124 and detachment of proximal detachment zone 124 are concerted. In other embodiments, locking of proximal detachment zone 124 occurs separately from detachment of proximal detachment zone 124.

The number of wires, braid angle, pore size, profile, diameter, shape etc. of the mesh of the distal self-expanding member 102 can vary depending on the application. For instance, a larger expanding member configured for a larger size aneurysm may have more wires than a smaller member. As mentioned above, the circumference of the distal self-expanding member 102 can have of any suitable shape (e.g., oval, square, etc.). In addition, the distal self-expanding member 102 can also have three-dimensional characteristics, including but not limited to, flat or generally even, conical, convex, concave, or any other shape depending on the application.

In some embodiments, the distal self-expanding member 102 mesh shape is fixed, such that upon exiting catheter 120, the distal self-expanding member 102 will return to its original, uncompressed state. In other embodiments, distal self-expanding member 102 mesh is adjustable such that the mesh cone angle can be adjusted. Upon exiting the catheter 120, the distal self-expanding member 102 mesh cone angle may be manipulated to any angle between 0° and 180°. The ability to control the angle of distal self-expanding member 102 mesh provides an additional level of control that may aid in delivery, positioning, and sealing processes. In some embodiments, distal detachable wire 114 may comprise additional wires or other components known in the art that may be used to control the mesh cone angle of distal self-expanding member 102.

In one embodiment, the diameter of the distal self-expanding member 102 and the end-to-end distance of the proximal anchoring member 110 can be between about 2-20 mm, and preferably about 5-7 mm. In the preferred embodiment, the diameter of the distal self-expanding member 102 and the end-to-end distance of the proximal anchoring member 110 are selected based upon at least by the size of the aneurysm. In particular, the diameter of the distal self-expanding member 102 is preferably about 1-2 mm larger than the neck of the target aneurysm. In some embodiments, the end-to-end distance of the proximal anchoring member 110 is preferably about 1-2 mm larger than the neck of the target aneurysm. The density of the wire mesh of the distal self-expanding member 102 can affect the performance of endovascular clip 100 in isolating the target aneurysm from incoming blood flow. In a preferred embodiment, the distal self-expanding member 102 comprises a high density of wires forming the mesh to reduce blood flow across the distal self-expanding member 102 and into the aneurysm.

Figure 12A:
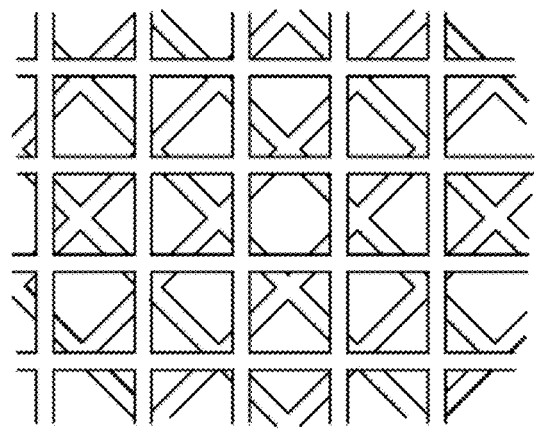
FIGS. 12A-12C depict multi-mesh layer embodiments of the distal self-expanding member.
Figure 12B:
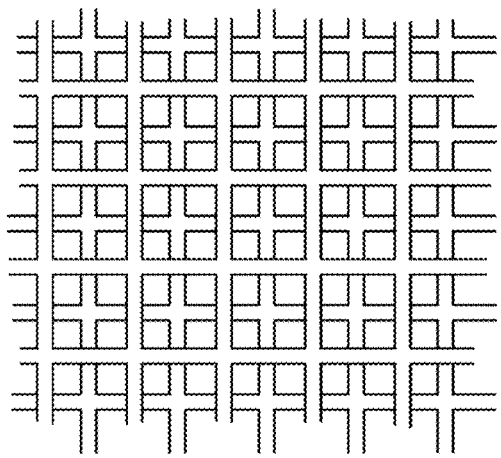

Distal self-expanding member 102 may comprise two or more mesh layers that can be offset against one another such that the wires or intersections of one mesh fully or partially obstructs the pores of the other mesh. FIGS. 12A and 12B show two exemplary embodiments of such offset configurations. As shown, the strands of each mesh are interpositioned so that the spaces between them are substantially blocked. This will further increase the density of the mesh of the distal self-expanding member 102 and decrease the size of these pores. In another embodiment, the arrangement and size of the mesh strands are configured to allow substantial or complete obstruction of the interstices.

Figure 12C:
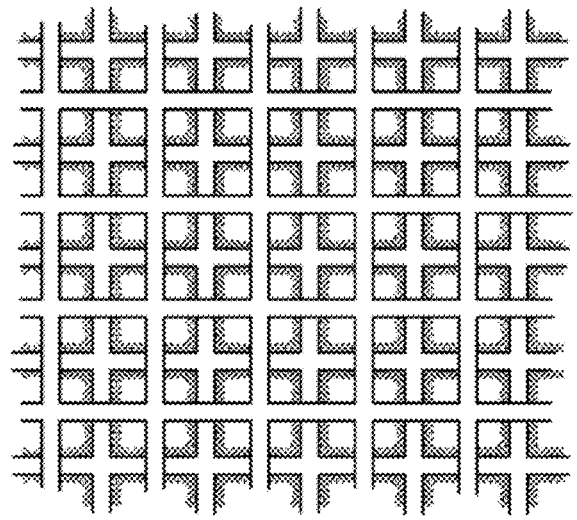

Additionally, referring to FIG. 12C, a distal self-expanding member 102 mesh can be coated with a material designed to produce the desired effect of obstructing the openings of the mesh. In a distal self-expanding member 102 that comprises more than one mesh layer, either or all mesh layers may be coated. A coating may be applied to an entire mesh, or be selectively applied to particular mesh strands. Such coating can include a swellable material that expands in volume when it comes in contact with a liquid or exposure to heat. An example of the swellable material includes, but are not limited to, a hydrogel or hydrogel foam. The swellable gel material can expand in volume as a result of hydration of it molecular structure, or by the filling of its pores with liquid (blood), or both.

The enlargement of the swellable coating or composition is designed to fill and close any remaining openings in the interstices of mesh layer or layers of distal self-expanding member 102. Accordingly, the neck of the aneurysm can be completely sealed with the clip 100 inserted in place, thereby blocking the blood flow into the aneurysm with the resultant aneurysm thrombosis. In one embodiment, the mesh of clip 100 may be less dense, i.e., less wires, than other clips that are not coated with the expandable coating. That is, the addition of the expansible material allows a clip 100 to perform the same function with less metallic wires, thereby providing a device with a lower profile for easier delivery to the aneurysm.

Suitable swellable materials include, but are not limited to: hydrogels; hydrophilic polymers with or without conjugated collagen as described in U.S. Pat. No. 5,413,791, the disclosure of which is incorporated by reference. In particular, conjugated collagen can include biocompatible, macroporous, hydrophobic hydrogel foams; and compressible, non-hydrophobic polymeric foam materials, such as polyurethane. A particularly preferred foam includes a water-swellable foam matrix formed as a macroporous solid comprising a foam stabilizing agent and a polymer or copolymer of a free radical polymerizable hydrophobic olefin monomer cross-linked as described in detail in U.S. Pat. Nos. 5,570,585 and 6,500,190, the disclosures of which are incorporated by reference.

Another suitable swellable material is a porous hydrated polyvinyl alcohol foam (PAF) gel prepared from a polyvinyl alcohol solution in a mixed solvent consisting of water and a water-miscible organic solvent, as described, for example, in U.S. Pat. No. 4,663,358, the disclosure of which is incorporated by reference.

In other embodiments, the mesh of distal self-expanding member 102 and the proximal controllable anchoring member 110 may be further coated or alternatively coated with additional materials, such as bioactive material which promote cell growth and attachment. The bioactive material may also be thrombogenic. Examples of the bioactive material include, but are not limited to, materials that increase cell attachment and/or thrombogenicity include both natural and synthetic compounds, e.g. collagen, fibrinogen, vitronectin, other plasma proteins, growth factors (e.g. vascular endothelial growth factor, "vEGF"), synthetic peptides of these and other proteins or peptides having attached RGD (arginine glycine-aspartic acid) residues, generally at one of both termini or other cell adhesion peptides, i.e., GRGDY, oligonucleotides, full or partial DNA constructs, natural or synthetic phospholipids or polymers with phosphorylcholine functionality. Agents which increase cell growth, and improve cell attachment and adhesion may be added or incorporated into any component of endovascular clip 100. In some embodiments, any or all components of endovascular clip 100 may be coated with stem cell. In some embodiments, stem cells are extracted from the patient then applied to the clip. In some embodiments, stem cells are extracted from the patient then applied at or near the aneurysm. Depositing the patient's stem cells at or near the aneurysm allows for accurate deposition of a high local concentration of differentiable cells.

In yet another embodiment, the distal self-expanding member 102 and the proximal controllable anchoring member 110 may be at least partially adapted to elute a pharmaceutical agent. The pharmaceutical agent can produce several biologic effect including but not limited to promotion of cell growth and attachment. As used herein, "eluting" includes, but not limited to, the following releasing, leaching, diffusing, or otherwise providing a pharmaceutical agent to a target area. Accordingly, the embodiments of the present disclosure allow for accurate delivery of the bioactive material and/or pharmaceutical agent to the aneurysm sac with minimal risks of migration of these material out of the aneurysm and into the parent vessel, where such migration would pose significant health risks to a patient.

Figure 8:
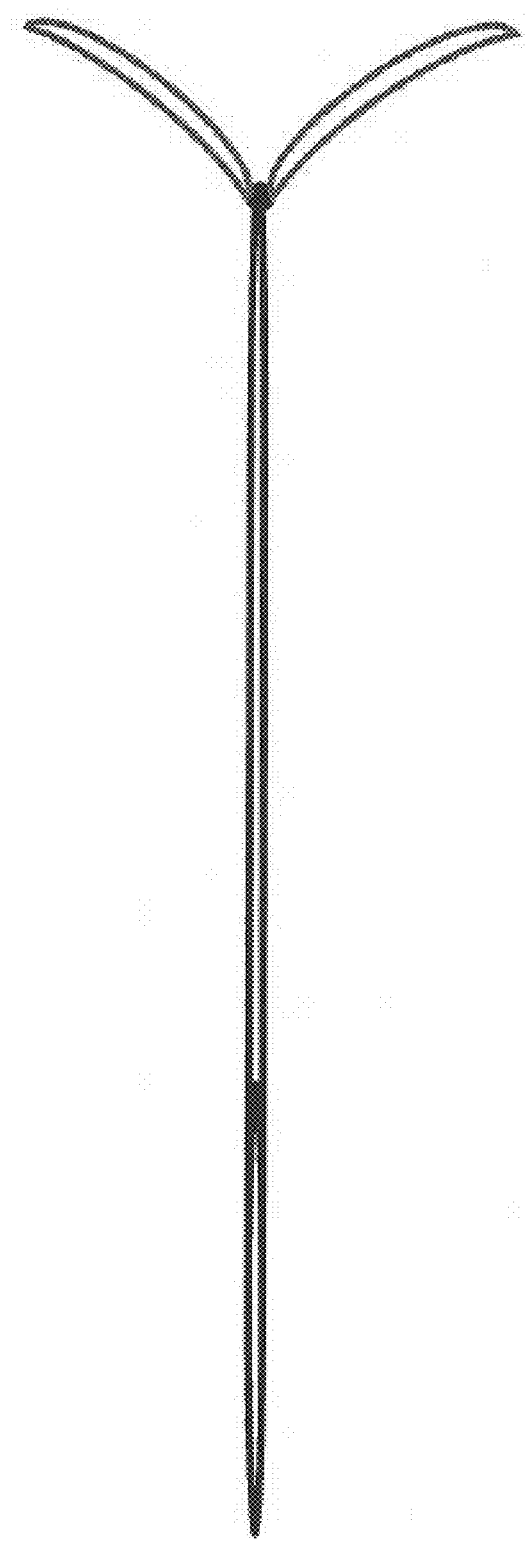
FIG. 8 is an illustration of a proximal anchoring member that comprises a pair of looped anchoring components.

Referring to FIG. 8A, clip 100 is inserted and moved to the aneurysm through the delivery catheter 120, which has proximal and distal catheter ends separated by a hollow catheter lumen preferably a cylindrical shaft. The distal end of catheter 120 is adapted for placement within the blood vessel inside an aneurysm sac. The clip 100 and concentric delivery wire system 112 fit within the lumen of the catheter 120.

The concentric delivery wire system 112 comprises distal detachable wire 114 and proximal detachable hypotube 116. The concentric delivery wire 112 system has a length sufficient to extend through the vascular system of the patient to place the clip 100 in the desired deployment location. In one embodiment, concentric delivery wire system 112 has a length of between about 50 cm-250 cm, more preferably a length of about 125-175 cm. The diameter of distal detachable wire 114 and/or proximal detachable hypotube 116 may be constant or may vary along the length of the delivery concentric delivery system 112. For example, the diameter of distal detachable wire 114 toward the proximal end away from the patient may be between about 0.2-1 mm, and preferably about 0.3-0.4 mm, while the diameter near the distal operative end may be between about 0.05-1 mm, and more preferably about 0.1-0.2 mm. Accordingly, the diameter of distal detachable wire 114 and/or proximal detachable hypotube 116 may taper from the proximal end to the distal end.

In one embodiment, the expandable clip 100 may include at least one radiopaque portion to facilitate visualization using, for example, one or more of fluoroscopy, computer tomography (CT) fluoroscopy, or the like. The radiopaque portion or portions can be a component of the expandable clip 100. In some embodiments, the distal attachment zone 126 is radiopaque. In some embodiments, proximal detachment zone 128 is radiopaque. In some embodiments, both distal attachment zone 126 and proximal detachment zone 128 are radiopaque. The radiopaque material can include platinum or tantalum DFT Nitinol or could be a separate radiopaque marker and/or material attached to or coated on at least a portion of the expandable member.

According to another aspect of the present disclosure, there is a method of treating an aneurysm, particularly a brain aneurysm using the endovascular clip 100. In one embodiment, an angiographic evaluation of the aneurysm is performed. Based on the anatomical data obtained, namely the measurements of the aneurysm neck dimensions in several planes, the shape and configuration of the aneurysm neck, the shape and branching pattern of the parent vessels, and the angle of attachment of the aneurysm to the parent vessels, a suitable clip 100 is selected. In one embodiment, the anatomical data provides data on which to select the shape and dimensions, including diameter, three-dimensional properties (e.g., concave, convex, flat), thickness, etc. of distal self-expanding member 102 and the proximal anchoring member 110.

Figure 3:
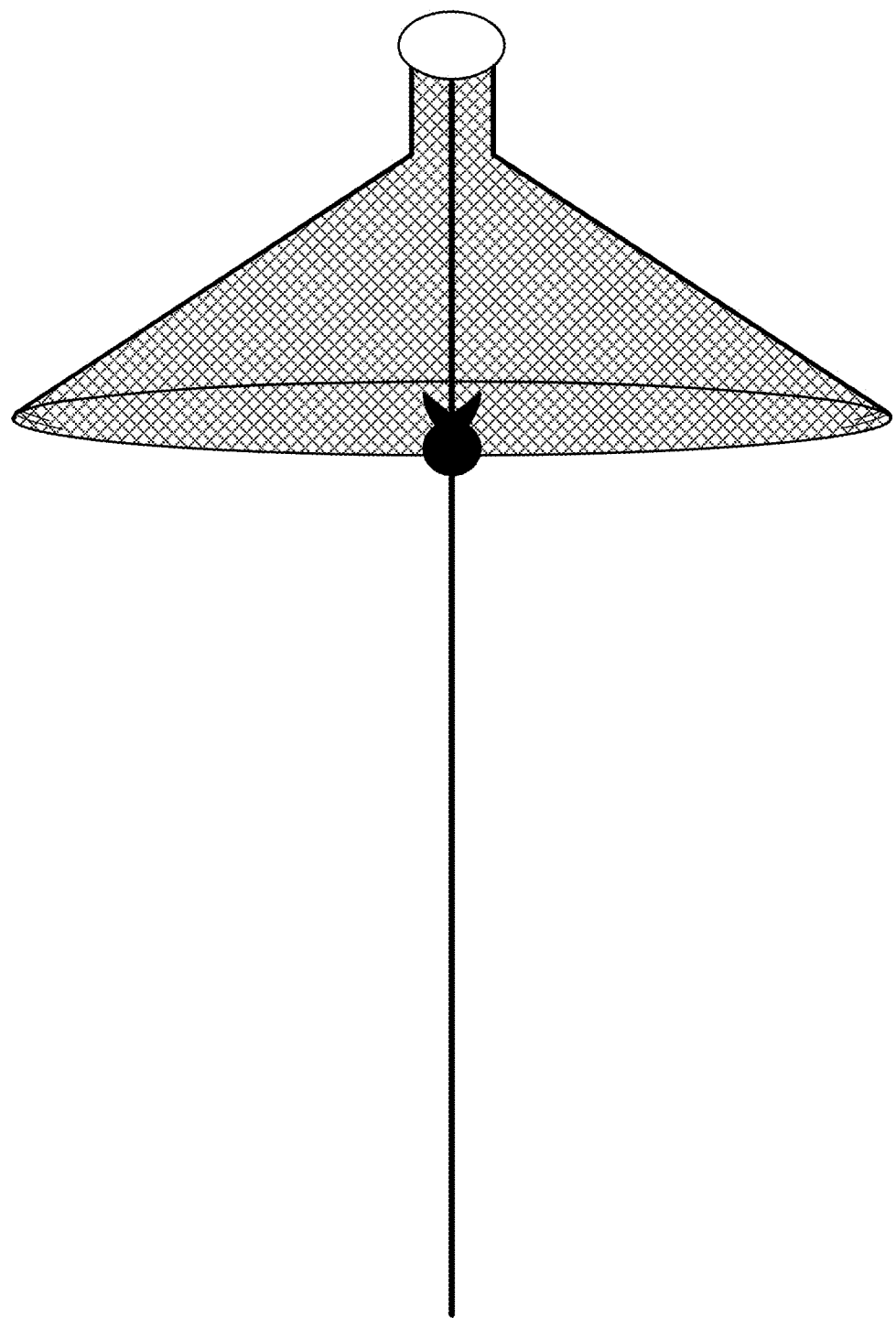
FIG. 3 is an image of an endovascular clip distal self-expanding member. The original uncompressed configuration of the distal self-expanding member mesh is conical in shape. A steering/detachment joint and locking edges are incorporated with distal detachable wire.
Figure 4:
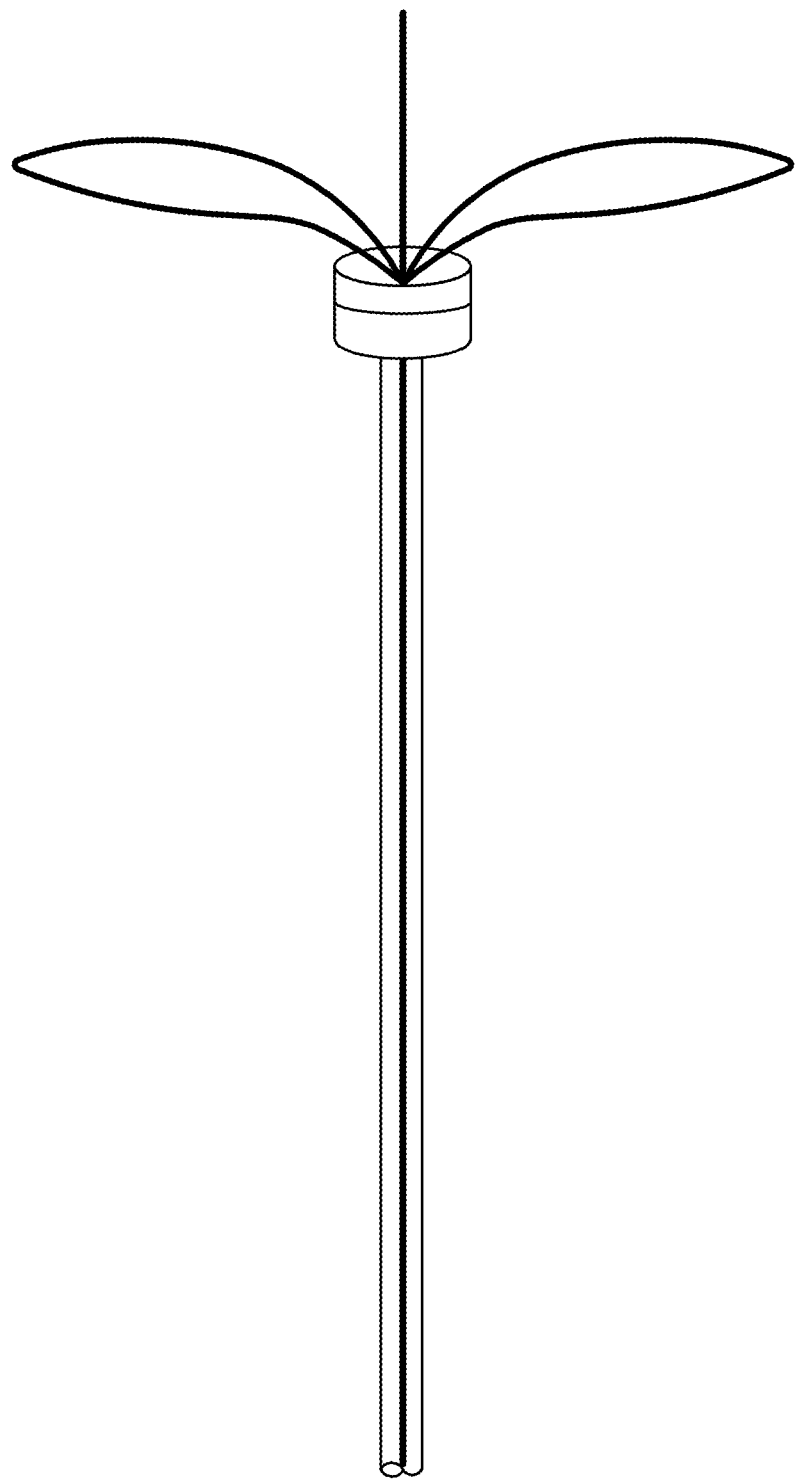
FIG. 4 is an image of a proximal anchoring member. The proximal anchoring member comprises a pair of looped anchoring members coupled to the proximal detachment zone. The proximal anchoring member is coupled to a proximal detachable hypotube. The distal detachable wire is emanating from the proximal detachable hypotube lumen.
Figure 11:
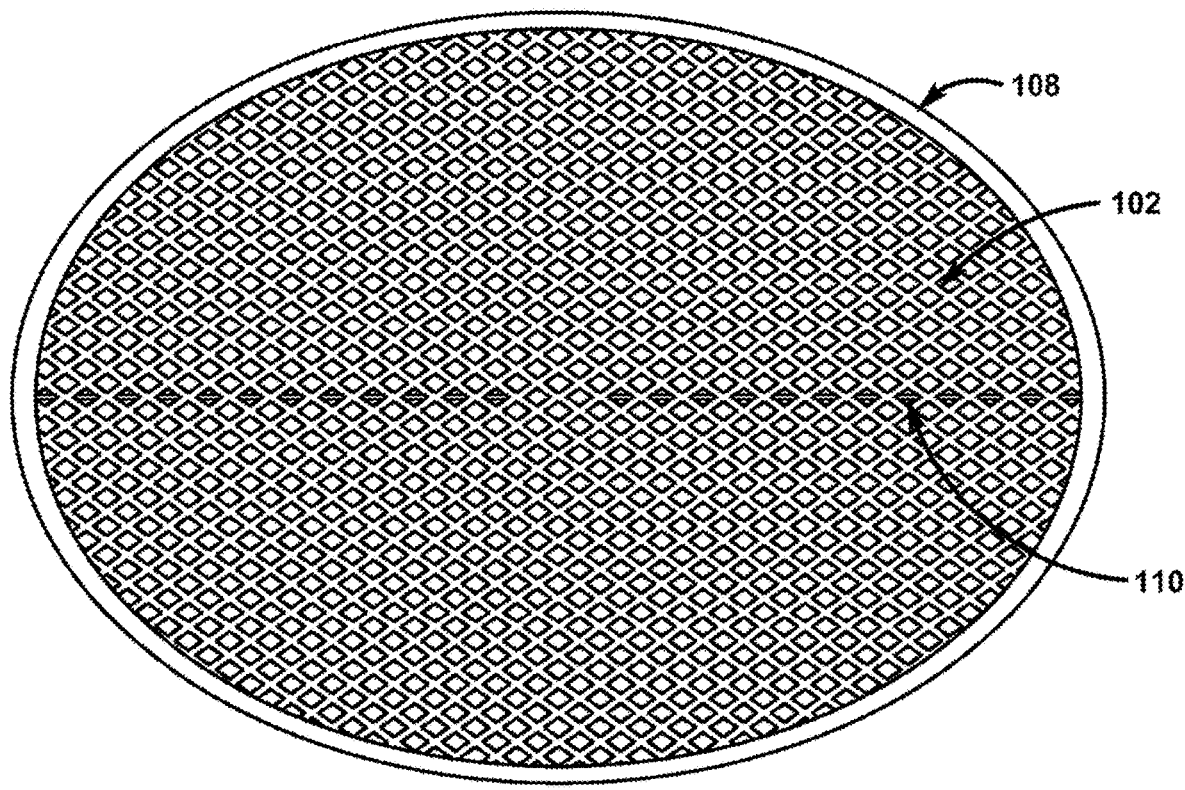
FIG. 11 is an illustration of an expanded self-expanding member that is reinforced by a reinforcing wire. The reinforcing wire is connected to opposite sides of peripheral frame.

For instance, referring to FIG. 9A, the depicted aneurysm is generally known as a bifurcation aneurysm, which is often difficult to treat with conventional means, such as coils and stents, due to the "T" configuration of the main artery. For this type of aneurysm, a clip with a concave distal self-expanding member, such as the one depicted in FIGS. 1-3, may be the most appropriate. On the other hand, for a side wall aneurysm, a clip 100 with a flat distal self-expanding member as depicted in FIG. 11, may be more appropriate.

Also, an aneurysm that is relatively smaller may benefit from a clip with only one lattice. While FIGS. 9A-9G show a bifurcation aneurysm in the brain, the embodiments of the present disclosure are applicable to other types of aneurysm occurring elsewhere in the body.

Figure 9D:
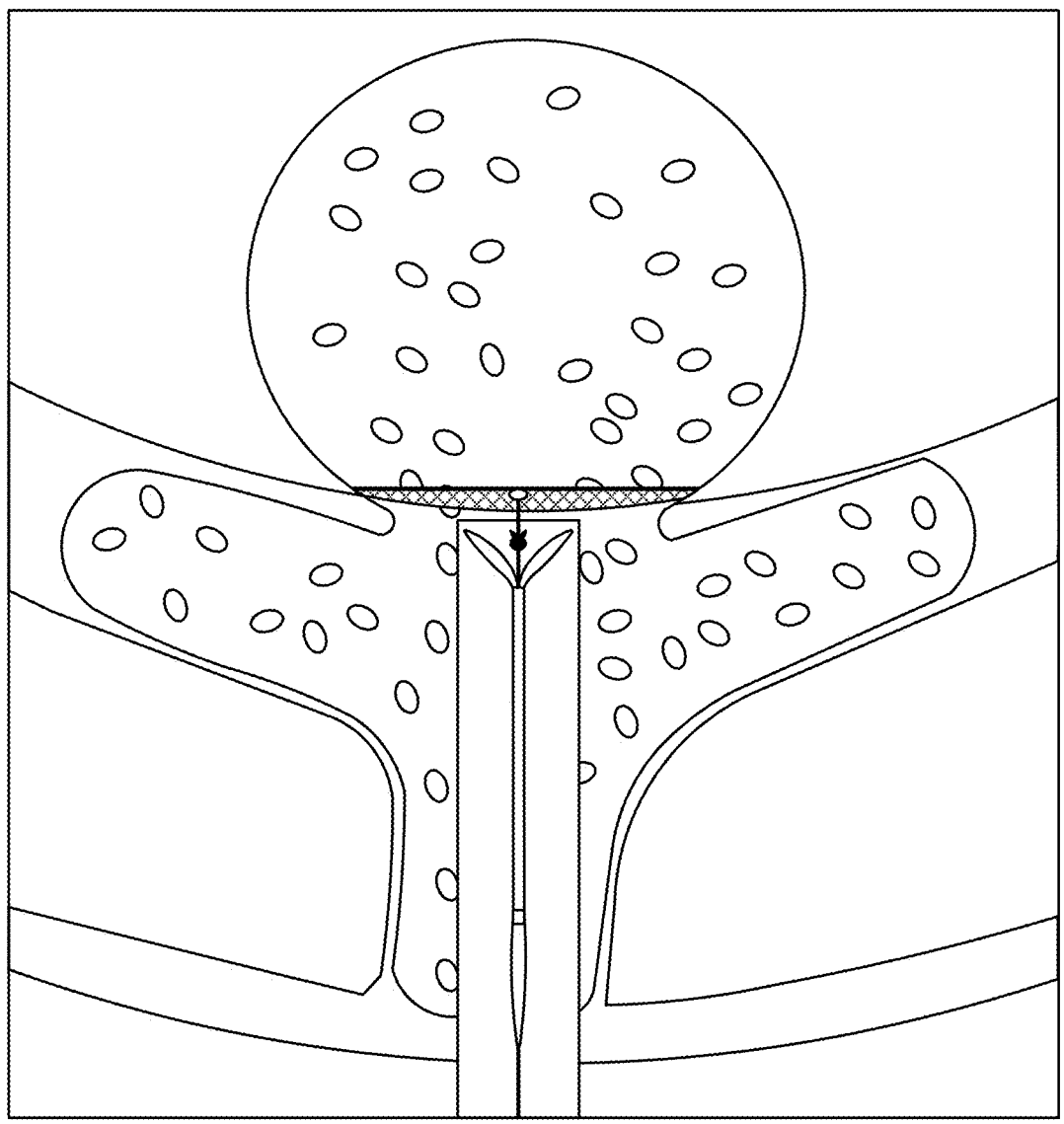

Referring to FIG. 9D, in some embodiments, the size of the distal self-expanding member 102 is slightly larger than the neck of the aneurysm. In some embodiments, the end-to-end distance of the proximal controllable anchoring member 110 is larger than the neck 404 of the aneurysm. Preferably, the diameter of the distal self-expanding member 102 and the end-to-end distance of the proximal anchoring member 110 is about 0.5 to 3 mm larger than the diameter of the neck, and more preferably about 1-2 mm larger. The slightly larger size allows the clip 100 to substantially or completely cover the neck of the aneurysm when the distal self-expanding member 102 and the proximal anchoring member 110 are fully deployed.

In some embodiments, suitable shapes of the distal self-expanding member 102 and the proximal anchoring member 110 are selected to conform to the anatomy of the aneurysm and parent vessel without significant deformation or stress on the walls of either the aneurysm or the vessel. In some embodiments, the distal self-expanding member 102 and proximal anchoring member 110 are adjustable such that the mesh cone angle and anchoring component angles may be adjusted before and/or during surgery.

In some embodiments, under life fluoroscopic imaging, the delivery catheter 114 is advanced over a wire to a position just inside the aneurysm sac. Referring to FIG. 9A, the selected clip 100 is loaded inside the proximal end of the catheter, where the clip 100 is longitudinally folded and constrained in the collapsed condition inside the lumen of catheter 120. Referring to FIG. 9B, using distal detachable wire 112, the distal self-expanding member 102 is pushed distally through the catheter lumen until the distal self-expanding member 102 is pushed beyond the distal end of the catheter 114 and into aneurysm 402. At this point, the expanding member 102 is fully released from the catheter 114 and expanded within the interior of the aneurysm 402 to its uncompressed, original shape. In embodiments having some superelastic material such as nitinol, the expansion is partially due to exposure to an activation mechanism such as temperature beyond the threshold temperature.

In some embodiments, referring to FIGS. 9B-9C, the distal member 102 is then pulled toward the neck so that it touches the inside walls of the aneurysm neck. While stabilizing the distal member 102 in position by holding the detachable delivery wire 112 in place, the catheter 120 may be slowly retracted to uncover the proximal anchoring member 110 outside the aneurysm neck. In some embodiments, the proximal detachable hypotube 116 may be used to push proximal anchoring member 110 out of catheter 120.

Figure 9E:
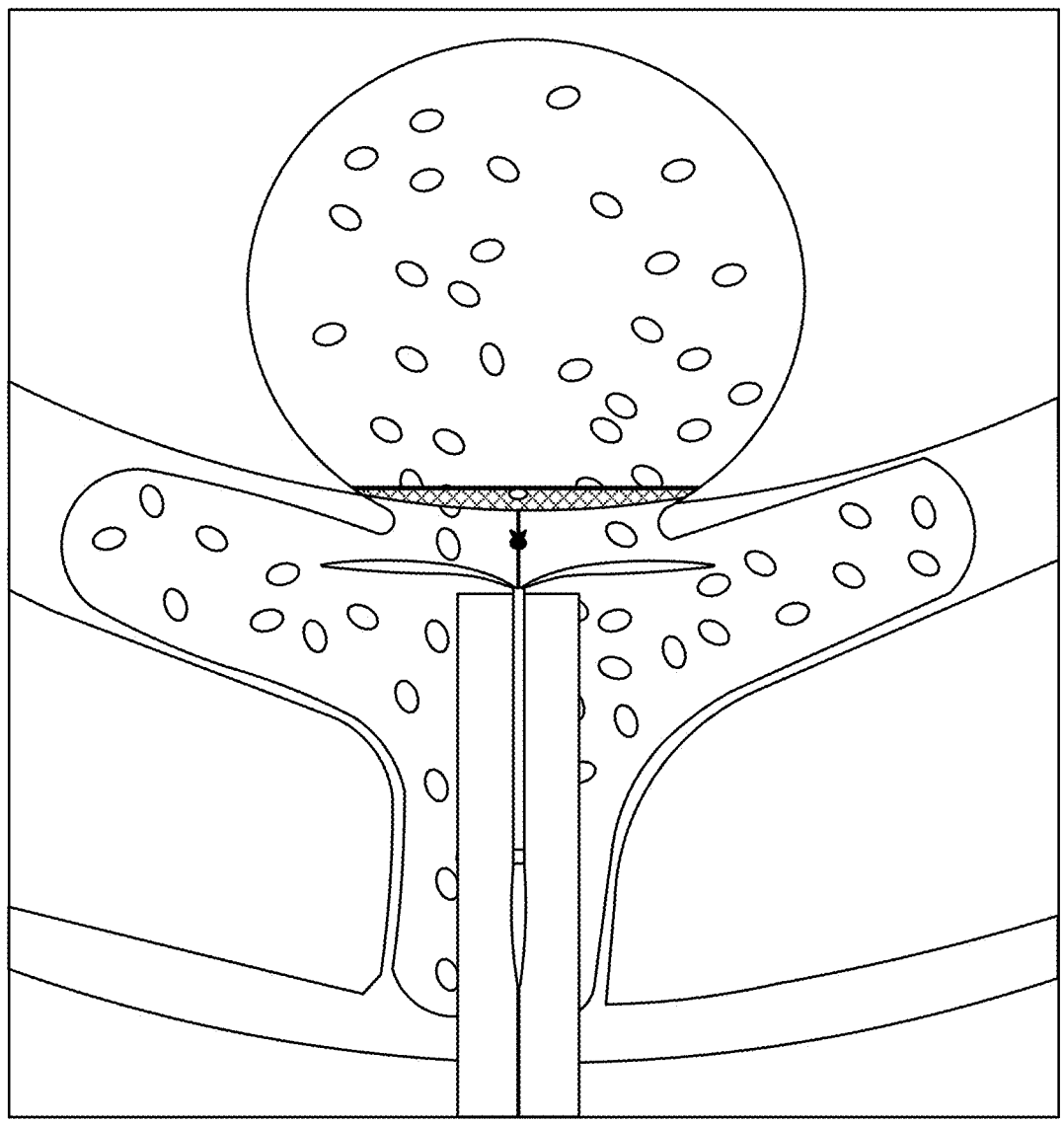
Figure 9F:
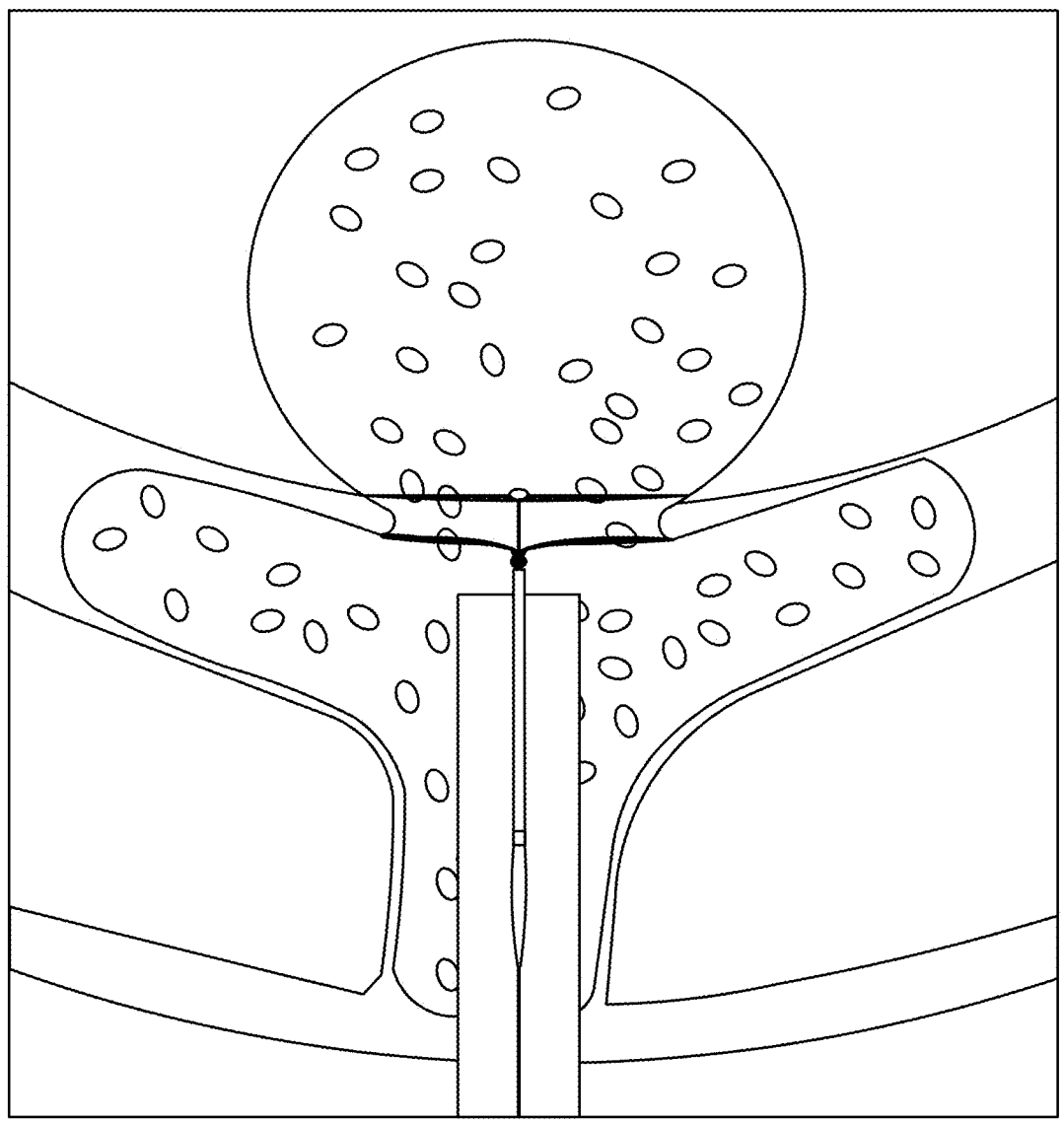
Figure 9G:
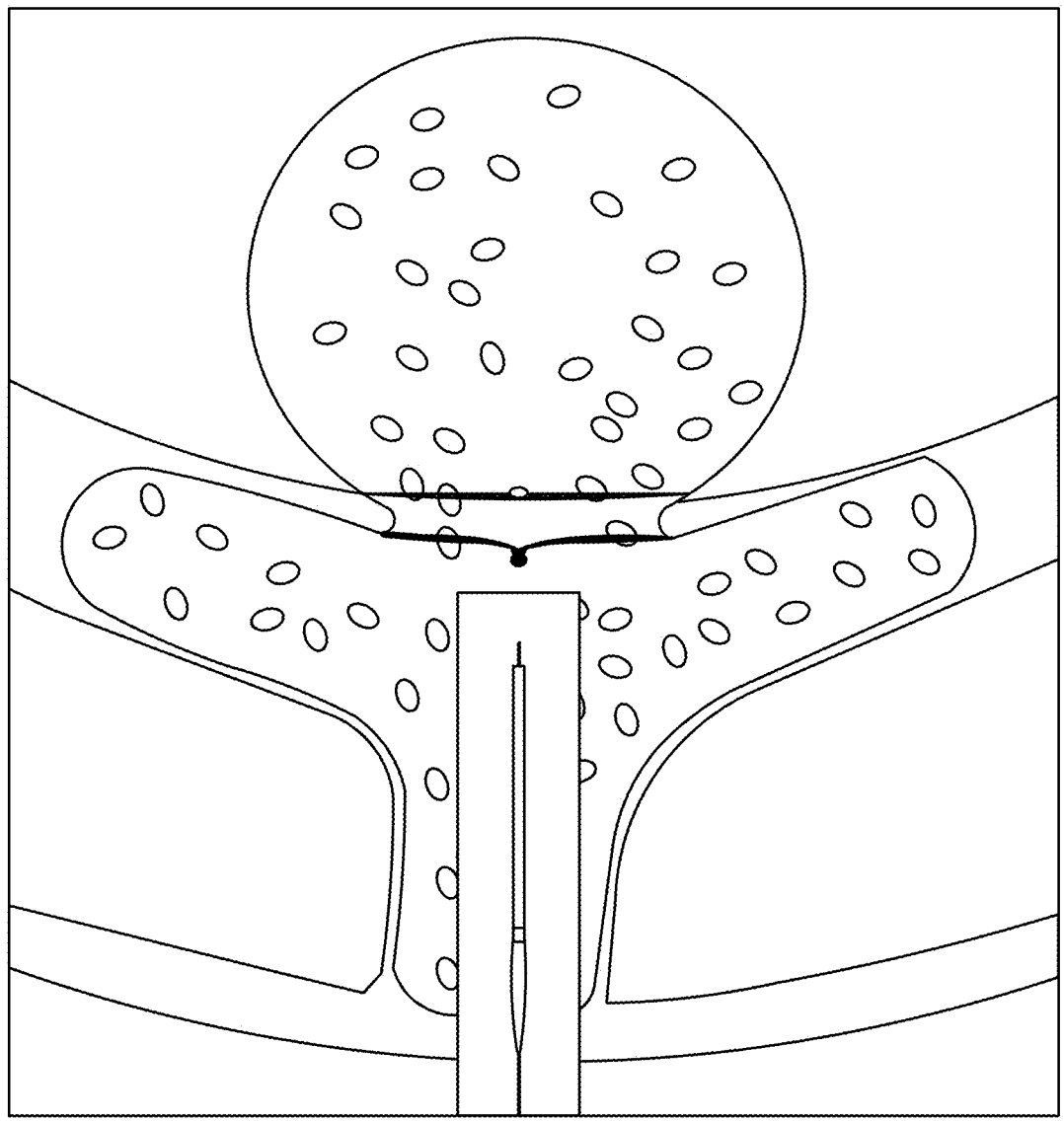
Figure 10:
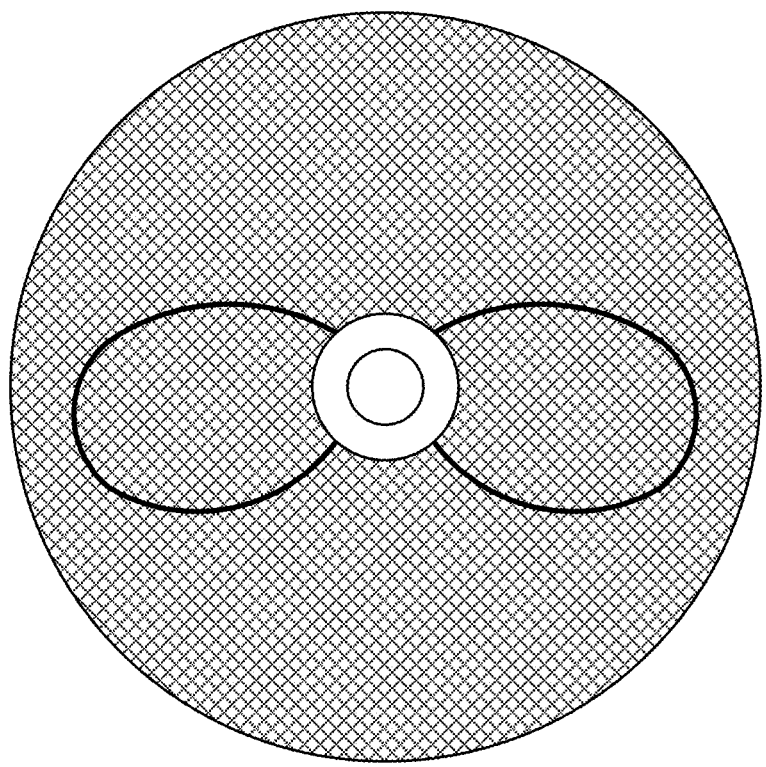
FIG. 10 is an axial view of a locked and detached clip.

Referring to FIG. 9E, the proximal anchoring member 110 is fully released from the catheter 120 and deploys to its original, uncompressed shape. In embodiments where the anchoring components 118 are adjustable, the anchoring component angles are adjusted to open the proximal anchoring member 110 such that the distance between radially terminal portions of anchoring components 118 is larger than the aneurysm neck radius. Referring to FIGS. 9E-9F, the proximal anchoring member 110 is manipulated toward aneurysm neck and the distal self-expanding member 102. After the anchoring components contact the aneurysm neck and the proximal detachment zone 128 passes over the locking edges 130, the proximal anchoring member 110 and distal self-expanding member 102 are locked into place. The proximal anchoring member 110 and distal self-expanding member 102 tightly squeeze the aneurysm neck from both sides such that the aneurysm neck is clinched between the proximal anchoring member 110 and the distal self-expanding member 102. Flattening of proximal anchoring member 110 anchoring components 118 provides a tensioning sealing force of the anchoring components against the aneurysm neck. In embodiments comprising a cone-shaped mesh, flattening of the distal self-expanding member 102 mesh provides a tensioning sealing force against the aneurysm neck. In embodiments comprising distal self-expanding member 102 reinforcing wires 106, the reinforcing wires generate or supplement the tensioning force of the distal self-expanding member 102.

In some embodiment, the mesh of distal self-expanding member 102, is further coated the bioactive material or eluting drugs as described above. In these embodiments, the bioactive material or eluting drugs can further accelerate occlusion and healing of the aneurysm by inducing thrombosis and scar formation as well as stimulation of the lining of the vessel to grow on and cover the disc with disc acting as a scaffolding upon which the cells grow which also lead to complete sealing the neck of the aneurysm and block the blood flow into the aneurysm with the resultant aneurysm thrombosis i.e., formation of clot, and closure. The healing of the aneurysm is achieved at least by the bioactive material or eluting drugs stimulating the healing of the lining of the blood vessel, which leads to encapsulation of the aneurysm. Throughout the life of the attached endovascular clip 100, the clip becomes incorporated into the aneurysm neck tissue. The self-expanding member 102 and proximal anchoring member 110 components act as scaffolds on and around which vasculature cells grow. As cell growth expands around the clip components, the clip 100 becomes incorporated and permanently anchored into the vessel wall.

As shown, the embodiments of the present disclosure allows for treatment of difficult aneurysms, such as a bifurcation aneurysm in the brain. In addition, the embodiments of the present disclosure also allows for delivery of materials, such as the bioactive materials and eluting drugs described above, to specific locations in the body to treat that particular site. In comparison, prior methods do not provide precise delivery of these materials, which expose the patient to significant risks because these bioactive materials and eluting drugs are dangerous if they are not delivered to the targeted location.

According to one aspect of the present disclosure, there is provided an endovascular clip comprising: a first deformable component; a second deformable component; each of said first and second deformable components comprises: a lattice comprising plurality of strands intersecting one another, wherein said intersecting strands form a plurality of interstices; a joint component attached to a portion of each of said first and second deformable components; wherein each of said first and second deformable components comprises a self-expanding material configured to have an original configuration and a deformed configuration; wherein said deformed configuration is generally perpendicular to said original configuration; wherein said self-expanding material is configured to change from said deformed configuration to said original configuration at least by exposure to an activating condition; wherein at least one of said first deformable component and said second deformable component is configured to extend across the neck of an aneurysm in the original configuration.

In one embodiment, said self-expanding material comprises nitinol. In another embodiment, said activating condition comprises a temperature above a defined threshold. In another embodiment, at least one of said first deformable component and said second deformable component further comprises a frame component, wherein said frame component circumscribes said lattice. In yet another embodiment, the diameter of said frame component is larger than the circumference of a portion of said strands of said lattice.

In another embodiment, at least one of said first deformable component and said second deformable component further comprises a reinforcing component having a first end and a second end, wherein both ends of said reinforcing component are attached to said frame member. In another embodiment, said lattice of at least one of said first deformable component and said second deformable component further comprises a swellable material configured to expand in volume upon exposure to an activating condition. In yet another embodiment, said swellable material is selected from the group consisting of hydrogel, hydrogel foam, hydrophilic polymers with conjugated collagen, hydrophilic polymers without conjugated collagen, porous hydrated polyvinyl alcohol foam (PAF) gel, and any combination thereof.

In another embodiment, said swellable material seals at least a portion of said interstices of the respective deformable component when exposed to the content of the aneurysm. In another embodiment, said lattice further comprises a bioactive material configured to promote cell growth. In another embodiment, said bioactive material comprises a thrombogenic material selected from the group consisting of collagen, fibrinogen, vitronectin, other plasma proteins, growth factors, peptides of said growth factors having attached RGD (arginine glycine-aspartic acid) residues, phospholipids, polymers with phosphorylcholine functionality, and any combination thereof.

In another embodiment, a portion of the strands from the lattice of said first deformable component obstructs a plurality of said interstices of said second deformable component. In another embodiment, the diameter of a first plurality of strands of said lattice are larger than the diameter of a second plurality of strands of said lattice. In another embodiment, said second plurality of strands are arranged to aid said change from said deformed configuration to said original configuration. In another embodiment, said second plurality of strands are located near the center of said lattice.

In another embodiment, said joint component is configured to be releasably attached to a delivery wire. In another embodiment, a portion of the neck of the aneurysm is sandwiched between a portion of said first deformable component and a portion if said second deformable component when said first deformable component and said second deformable component are extended across the neck of an aneurysm. In another embodiment, the medical device further includes a radiopaque material. In yet another embodiment, at least one of said first deformable component and said second deformable component has a shape selected from the group consisting of circular, oval, square, rectangular, concave, convex, generally leveled, and any combination thereof.

According to another aspect of the present disclosure, there is provided an endovascular clip comprising: a first deformable component consisting of a first frame component and a first reinforcing component; wherein a portion of said first frame component is attached to a portion of said reinforcing component; a second deformable component comprising a lattice having a plurality of strands intersecting one another, wherein said intersecting strands form a plurality of interstices; a joint component attached to a portion of each of said first and second deformable components; wherein each of said first and second deformable components comprises a self-expanding material configured to have an original configuration and a deformed configuration; wherein said deformed configuration is generally perpendicular to said original configuration; wherein said self-expanding material is configured to change from said deformed configuration to said original configuration at least by exposure to an activating condition; wherein at least one of said first deformable component and said second deformable component is configured to extend across the neck of an aneurysm in the original configuration.

In one embodiment, said self-expanding material comprises nitinol. In another embodiment, said activating condition comprises a temperature above a defined threshold. In another embodiment, said lattice further comprises a swellable material configured to expand in volume upon exposure to an activating condition. In another embodiment, said swellable material is selected from the group consisting of hydrogel, hydrogel foam, hydrophilic polymers with conjugated collagen, hydrophilic polymers without conjugated collagen, porous hydrated polyvinyl alcohol foam (PAF) gel, and any combination thereof. In another embodiment, said swellable material seals at least a portion of said interstices of the respective deformable component when exposed to the content of the aneurysm. In another embodiment, said lattice further comprises a bioactive material configured to promote cell growth. In another embodiment, said bioactive material comprises a thrombogenic material selected from the group consisting of collagen, fibrinogen, vitronectin, other plasma proteins, growth factors, peptides of said growth factors having attached RGD (arginine glycine-aspartic acid) residues, phospholipids, polymers with phosphorylcholine functionality, and any combination thereof. In another embodiment, said joint component is configured to be releasably attached to a delivery wire. In another embodiment, a portion of the neck of the aneurysm is sandwiched between a portion of said first deformable component and a portion if said second deformable component when said first deformable component and said second deformable component are extended across the neck of an aneurysm. In yet another embodiment, the medical device further includes a radiopaque material.

According to another aspect of the present disclosure, there is provided a method for treating an aneurysm comprising the steps of: extending a first deformable component of an endovascular clip within an aneurysm across a portion of the neck of said aneurysm; extending a second deformable component of said endovascular clip across a portion of the neck of said aneurysm; wherein each of said first and second deformable components comprises: a lattice comprising plurality of strands intersecting one another, wherein said intersecting strands form a plurality of interstices; wherein a portion of first and second deformable components are attached to a joint component of said endovascular clip; wherein each of said first and second deformable components comprises a self-expanding material configured to have an original configuration and a deformed configuration; wherein said deformed configuration is generally perpendicular to said original configuration; wherein said self-expanding material is configured to change from said deformed configuration to said original configuration at least by exposure to an activating condition; wherein at least one of said first deformable component and said second deformable component is configured to extend across the neck of an aneurysm in the original configuration.

In one embodiment, the method includes the step of delivering a swellable material configured to expand in volume upon exposure to an activating condition to the aneurysm by coating a portion of at least one of said first and second deformable components with said swellable material. In another embodiment, said swellable material is selected from the group consisting of hydrogel, hydrogel foam, hydrophilic polymers with conjugated collagen, hydrophilic polymers without conjugated collagen, porous hydrated polyvinyl alcohol foam (PAF) gel, and any combination thereof.

In another embodiment, the method includes the step of: delivering a bioactive material configured to promote cell growth to said aneurysm by coating a portion of at least one of said first and second deformable components with said bioactive material. In one embodiment, said bioactive material comprises a thrombogenic material selected from the group consisting of collagen, fibrinogen, vitronectin, other plasma proteins, growth factors, peptides of said growth factors having attached RGD (arginine glycine-aspartic acid) residues, phospholipids, polymers with phosphorylcholine functionality, and any combination thereof.

Referring to FIGS. 13A-13D, the endovascular clip 500 comprises a distal self-expanding disc or member 502 and a proximal self-expanding disc or member 504. The self-expanding members 502 and 504 are joined to a connecting joint 506. In the preferred embodiment, each of self-expanding members 502 and 504 substantially comprises a single layer of intersecting wires or strands forming a mesh having a plurality of interstices. The strands or wires may comprise a superelastic and/or self-expanding material. In particular, superelastic and/or self-expanding material should have properties that allow it to have a deformed shape under one condition and to recover its original shape prior to deformation upon exposure to an activation mechanism. Preferably, the material can include a memory-shaped heated alloy such as nitinol, or nickel titanium, which is a metal alloy of nickel and titanium. Nitinol alloys exhibit two closely related and unique properties: shape memory and superelasticity. Shape memory refers to the ability of nitinol to undergo deformation at one temperature, then recover its original, un-deformed shape upon heating above its "transformation temperature." That is, nitinol alloy has a biased self expanded condition and may be compressed into a collapsed or deformed condition before use. During use, it may be exposed to temperature above the transformation threshold, thereby causing it to revert back to its un-deformed shape.

In certain embodiments, in addition to self-expanding material, the strands of members 502 and 504 may comprise any desired material or combination of materials, including, but not limited to, a metal, an alloy, a composite, a polymer, and the like. For example, a plurality of strands may comprise nitinol, stainless steel, cobalt chromium, platinum, titanium, plastic, or any combination thereof. The strands may each have a diameter preferably between about 5-200 microns, and more preferably between 40 to 60 microns. In other embodiments, the diameter of the strands are configured to according to the selected size of the endovascular clip 500.

In another embodiment, one or both of the self-expanding discs 502 and 504 can comprise more than one layer of wire mesh. The pattern of the mesh may be regular or irregular, as long as the pattern of the strands of the mesh form a plurality of interstices. For instance, referring to FIGS. 13A and 13B, the strands of the mesh may be perpendicular to one another such that squares or rectangular openings are formed. In other embodiments, circular or irregularly shaped openings may be formed. In one embodiment, the square or rectangular openings may be of uniform dimensions or they may be of different dimensions. For example, the strands closer to the center of the self-expanding disc, e.g., member 502 or 504, may be placed closer to one another to form smaller openings, as compared to larger interstices may be formed by strands placed further apart from one another near the edge of the self-expanding disc, or vice versa. Additional aspects of the density of the strands of the mesh are further discussed below. Preferably, the number and placement of the strands are configured to provide a mesh with a minimum amount of material that is still sufficient to allow the endovascular clip 500 to serve at least as a physical barrier to isolate the aneurysm from the flow of the parent artery. A self-expanding disc with a minimal yet sufficient mesh provides a lighter endovascular clip that allows for better maneuverability when it is being inserted and placed in the patient.

Referring to FIGS. 13A-13E, the mesh can be reinforced by a ring or frame 508 that is attached to the periphery of self-expanding members 502 and 504. The frame 508 can also comprise a superelastic and/or self-expanding material, such as nitinol, or any other material that provides similar superelasticity properties. In particular, referring to FIGS. 13B and 13E, the peripheral frame 508 has a deformed or compressed shape with a smaller diameter in FIG. 13B than the un-deformed, original shape shown in FIG. 13E. The peripheral frame 508 may comprise a single strand that has a larger diameter than the strands of the mesh. In one embodiment, the diameter of the peripheral frame 508 is at least double the diameter of the strands of the mesh of self-expanding discs 502 and 504. In another embodiment, the diameter of peripheral strand 508 is between about 10-500 microns. More preferably, the diameter of the peripheral frame 508 is about 80-120 microns The peripheral frame 508 can have different un-deformed shapes such as circular, oval, rectangular or any other regular or irregular shapes that may be suitable to the application, e.g., appropriate fit with the neck of a particular aneurysm.

Figures 13A, 13B:
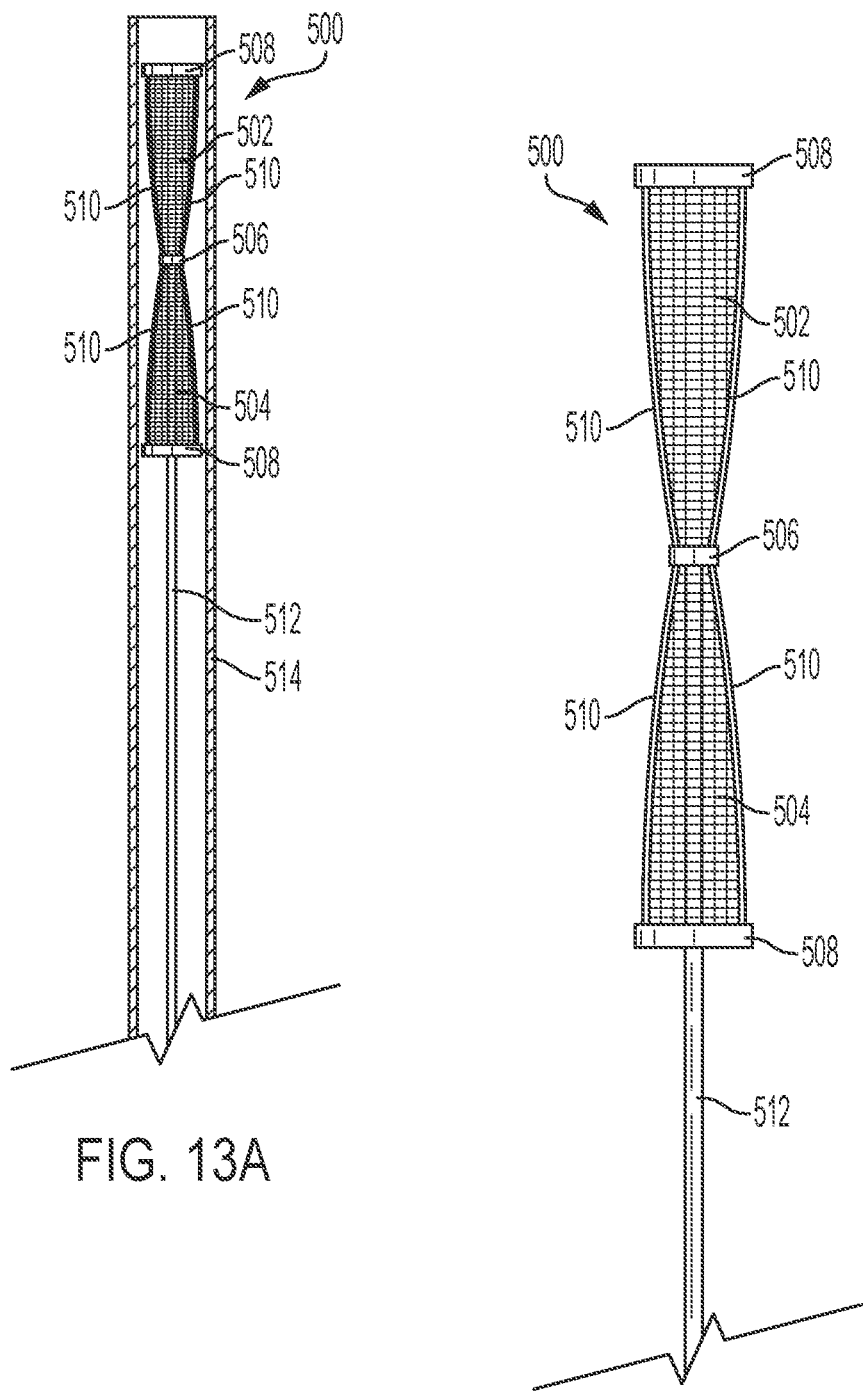
FIG. 13A is a side view of a preferred embodiment of the present disclosure in a collapsed state within a catheter.
FIG. 13B is a side view of the preferred embodiment of the present disclosure in a collapsed state.
Figures 13C, 13D:
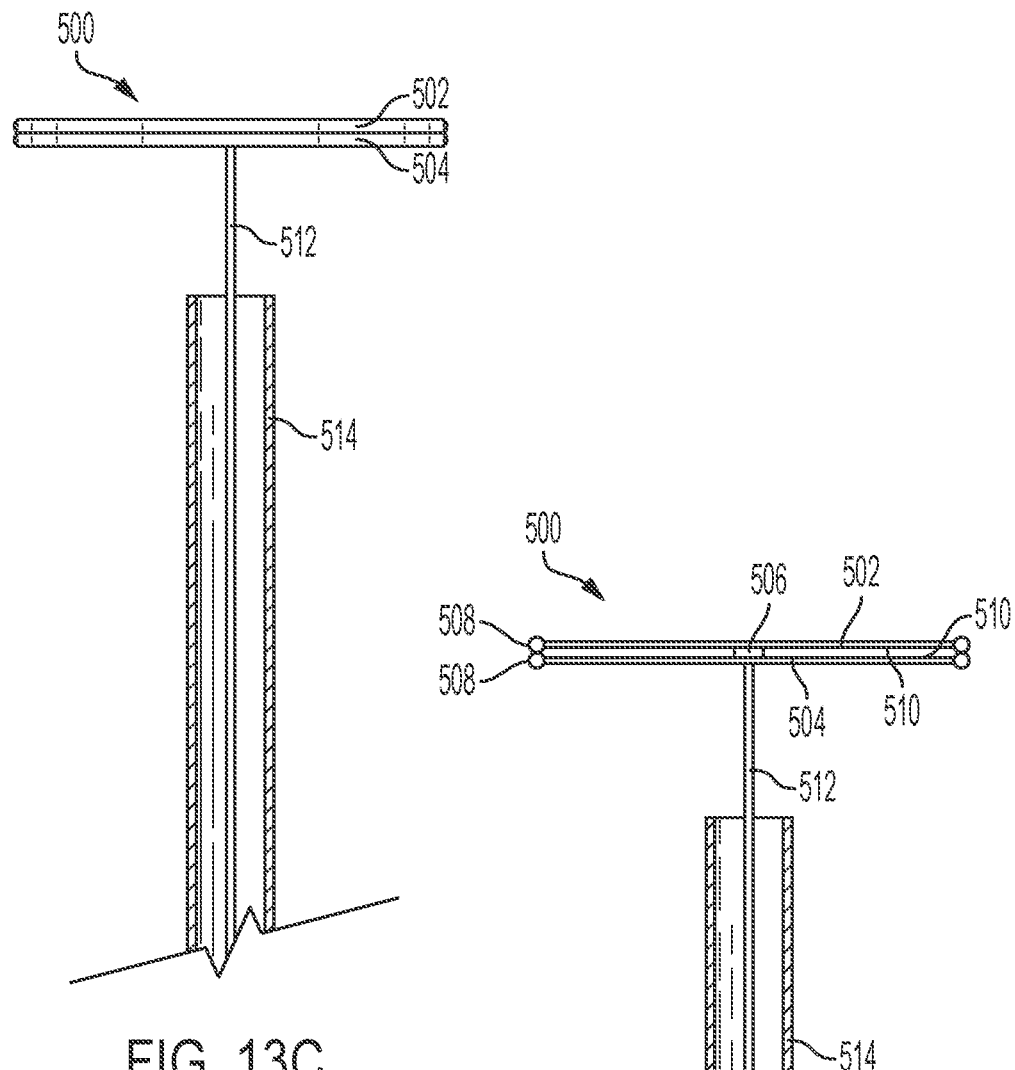
FIG. 13C is a side view of the preferred embodiment of the present disclosure in a non-collapsed state and attached to a delivery wire.
FIG. 13D is a cross-section of the preferred embodiment of the present disclosure in a non-collapsed state and attached to a delivery wire.
Figure 13E:
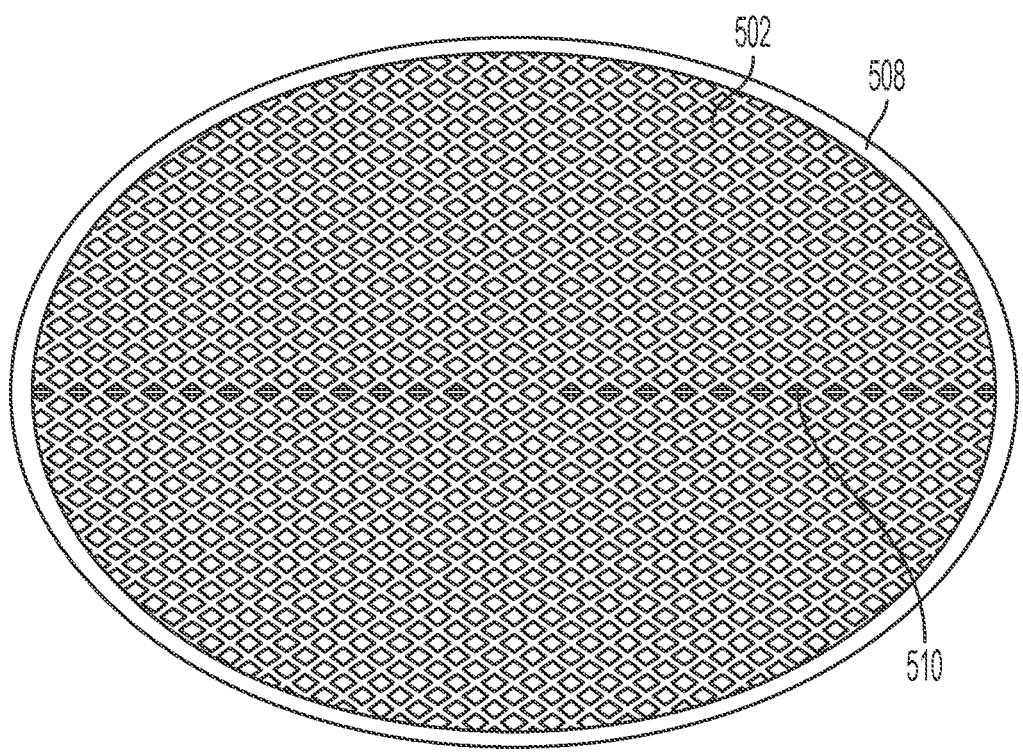
FIG. 13E is a top view of the preferred embodiment of the present disclosure in a non-collapsed state.

FIGS. 13C and 13D show the endovascular clip 500 is in its original configuration, and FIGS. 13A and 13B show the endovascular clip 500 is in the deformed configuration. As shown, the deformed configuration of the self-expanding members 502 and 504 are generally perpendicular to the original configuration of the self-expanding members 502 and 504.

Referring to FIGS. 13A-13D, the two self-expanding members 502 and 504 are connected to each other by the connecting joint 506 disposed between the self expanding members 502 and 504. The connecting joint 506 can be made of any desired material or combination of materials, including, but not limited to, a metal, an alloy, a composite, a polymer, and the like. In one embodiment, the connecting joint 506 may be formed from the same material, e.g., nitinol, as that of the self-expanding members 502 and 504, such that a portion of the mesh of at least one self-expanding member 502 or 504, and/or reinforcing wire 510 (discussed further below), is integral with a portion of the connecting joint 506. Alternatively, the self-expanding members 502 and 504 may be welded to the connecting joint 506. In other embodiments, the self-expanding members 502 and 504 may be attached to connecting joint 506 through appropriate means. In another embodiment, the connecting joint 506 can comprise a radiopaque material. Due to the superelastic properties of the mesh of self-expanding members 502 and 504, the integrity of the material attachment sites between the self-expanding members 502 and 504 and the connecting joint 506 are preferably minimally affected by the folding and unfolding of the self-expanding members 502 and 504 during their transition between the original and deformed conditions.

In one embodiment, the connecting joint 506 has a diameter between about 0.1-2 mm. Referring to FIGS. 13A-13D, the connecting joint 506 preferably should have a diameter that is as small as possible but still sufficient to allow delivery wire 512 to attach to connecting joint 506 and deliver clip 500 to the desired location in the patient. Accordingly, in another embodiment, the diameter of the connecting joint 506 is slightly larger than the diameter of the delivery wire 512. The delivery wire 512 may be attached to the proximal surface of the connecting joint 506 by various means that allow the user to selectively release the connecting joint 506 from the delivery wire 512 known to those skilled in the art. For example, suitable release mechanisms may include mechanical, chemical, electrolytic, temperature-sensitive, remotely-triggered, or other type of release means. One exemplary mechanical release mechanism is a ball mount.

The height of the joint 506 and angle and location of attachment of the self expanding members 502 and 504 to the connecting joint 506 are configured to keep the self expanding members 502 and 504 in close parallel proximity, where they are preferably touching one another. In the preferred embodiment, the opposing surfaces, whether the mesh surface and/or frame surface, of the self expanding members 502 and 504 are configured to gently press against each other. This allows for at least the edge of self-expanding members 502 and 504 to slightly squeeze and attach to the neck of the aneurysm when the self-expanding members 502 and 504 have recovered to its original horizontal position, such as that shown in FIGS. 16E and 16F. In one embodiment, the endovascular clip 500 is anchored at the desired location by the slight squeeze and attachment of the self-expanding members 502 and 504. In other embodiments, it is envisioned that other anchoring means, such as additional leg support structures, may be used to supplement the attachment of the self-expanding members 502 and 504 to the neck of the aneurysm.

In one embodiment, the mesh of at least one self-expanding member, 102 or 504, can further be reinforced by a reinforcing wire 510. Referring to FIGS. 13A, 13B, and 13D, in a preferred embodiment, the reinforcing wire 510 is connected at both ends to the peripheral frame 508. The central portion of the reinforcing wire 510 is attached to the connecting joint 506. The substantial portion of the length of the reinforcing wire 510 is attached to the surface of certain strands of the mesh of the respective self-expanding member, 502 or 504. The reinforcing wire 510 may also made of superelastic and/or self-expanding material, such as memory-shaped heated alloy, e.g., nitinol. As discussed above, the reinforcing wire 500 may be formed from the same material as that of the self-expanding members 502 and 504 and connecting joint 506 such that at least a portion of each of these components may be integral with one another. In one embodiment, the reinforcing wire 510 may have a larger diameter than the strands of the mesh. Preferably, the diameter of the reinforcing wire 510 is between about 10-500 microns, and more preferably a diameter of about 50-75 microns. In another embodiment, both self-expanding discs 502 and 504 includes at least one reinforcing wire 510. In embodiments where one or both self-expanding members 502 and 504 include(s) more than one reinforcing wires 510, the wires may be placed to evenly divide the surface of the respective self-expanding disc. For instance, if there are two reinforcing wires 510 for one self-expanding members, they may be placed perpendicular to one another with the intersection being at or near connecting joint 506.

When the clip 500 is in its compressed or deformed state, it is constrained inside the delivery catheter 514. Referring to FIG. 13B, in embodiments having at least one reinforcing wire for each self-expanding member, the reinforcing wires 510 are folded up in a generally longitudinal fashion proximate to the catheter shaft. Referring to FIGS. 16B-16E, once the self-expanding members, e.g. 502, of clip 500 are deployed out of the distal end of the catheter 514, the reinforcing wires 510 move into their biased or original alignment toward each other, thereby bringing the mesh and/or the peripheral frame 508 of each self-expanding member, 502 or 504, toward one another and into a horizontal position.

Alternatively, in an embodiment without reinforcing wire 510, this biased alignment can be otherwise achieved without the need for a central reinforcing wire 510. For instance, in one embodiment, the biased or unconstrained horizontal alignment of the self-expanding members 502 and 504 can be achieved by having some strands of the mesh that are slightly thicker to impart additional strength to the self-expanding member. The thicker wires impart greater strength without significantly increasing the delivery profile of clip 500 while the thinner wires offer support while providing the desired strand density for the mesh and without requiring additional material or increasing the delivery profile. Various permutations are available where in some embodiments, both or one of the self-expanding members 502 and 504 can be without a frame 508 and/or reinforcing wire 510. The different thickness or density arrangements of the strands of each of the self-expanding members 502 and 504 can be adjusted to optimize the member's recovery to the horizontal biased position as described.

The self-expanding members 502 and 504 are configured with desired deployment characteristics and configured to provide sufficient flexibility for tracking through a possibly tortuous vascular system of an individual, such as the intracranial vascular system. The clip 500 may be inserted into a blood vessel in any suitable manner, such as through the use of endovascular, percutaneous, or other minimally invasive surgical techniques. They may be formed in any desired manner, including, but not limited to, braiding, welding, molding, weaving, laser-cutting a tube or sheet, and the like.

The number of wires, braid angle, pore size, profile, diameter, shape etc. of the mesh of the self-expanding members 502 and 504 can vary depending on the application. For instance, a larger expanding member configured for a larger size aneurysm may have more wires than a smaller member. As mentioned above, the circumference of the self-expanding members 502 and 504 can have of any suitable shape (e.g., oval, square, etc). In addition, the self-expanding members 502 and 504 can also have three-dimensional characteristics, including but not limited to, flat or generally even, conical, convex, concave, or any other shape depending on the application. Preferably, the shapes of the circumference and three-dimensional characteristics of both self-expanding members 502 and 504 are the same.

In one embodiment, the diameter of the self-expanding members can be between about 2-20 mm, and preferably about 5-7 mm. In the preferred embodiment, the diameter of the self-expanding members 502 and 504 are determined at least by the size of the aneurysm. In particular, the diameter of the self-expanding members 502 and 504 is preferably about 1-2 mm larger than the neck of the target aneurysm. The density of the wire mesh of the self-expanding members 502 and 504 can affect the performance of the clip 500 in isolating the target aneurysm from incoming blood flow. In the preferred embodiment, the self-expanding members 502 and 504 have high density of wires forming the mesh to reduce blood flow across the self expanding members 502 and 504 and into the aneurysm.

Figure 14:
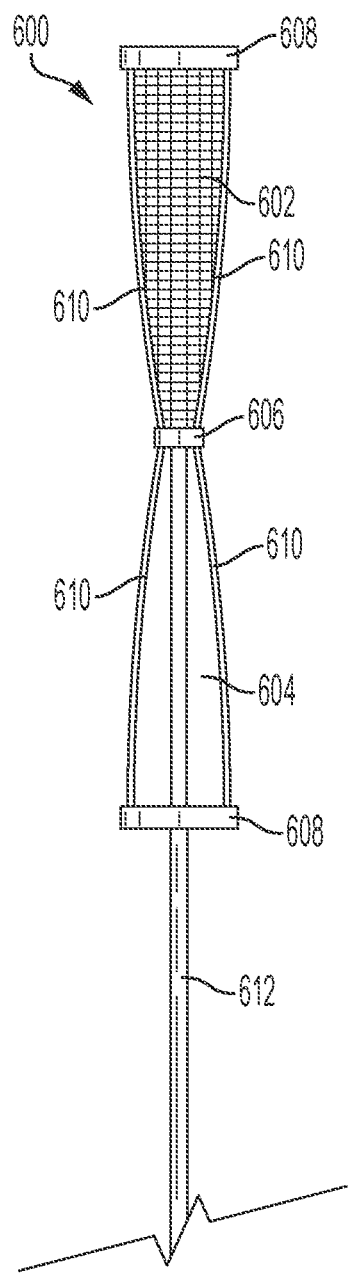
FIG. 14 is a side view of another embodiment of the present disclosure in a collapsed state.

Referring to FIG. 14, according to another aspect of the present disclosure, the swellable material coated on one lattice, preferably the distal lattice, forms a sufficient barrier to prevent further blood flow into the aneurysm and promote healing such that a second lattice is not necessary. As shown by FIG. 14, endovascular clip 600 is similar to clip 500 of FIGS. 16A-16E, except the distal self-expanding disc 602 includes a lattice and proximal self-expanding disc 604 includes only reinforcing wire 610 and frame 608. The frame 608 of the proximal self-expanding disc 604 slightly presses against frame 608 of distal self-expanding disc 602 to anchor clip 600 to the neck of an aneurysm while the lattice of the proximal self-expanding disc 604, having its interstices closed by the swellable material, serves as the barrier. The reinforcing wire 610 of the proximal self-expanding member 604 provides support and connects the frame 608 of the proximal self-expanding member 604 to the joint 606. This aspect of the present disclosure allows for clips that are lighter and require less material to make. In other embodiments, the distal self-expanding disc 602 need not include frame 608 and/or reinforcing wire 610 as discussed above with respect to clip 500. The clip 600 may be anchored to the neck of the aneurysm by the pressure between frame 608 of the proximal self-expanding member 604 and the lattice of the distal self-expanding disc 602, where the diameter and/or density of the lattice strands close to the peripheral distal self-expanding disc 602 are greater than that of the strands closer to the center. Joint 616 functions similarly to joint 506 and allows for releasable engagement with delivery wire 612. Other features discussed herein with respect to clip 500, such as dimensions, materials, strand density, strand diameter, shape of the self-expanding members, etc., are also applicable to clip 600.

Referring to FIGS. 13A-13D, clip 500 is inserted and moved to the aneurysm through the delivery catheter 514, which has proximal and distal catheter ends separated by a hollow catheter lumen preferably a cylindrical shaft. The distal end of catheter 514 is adapted for placement within the blood vessel inside an aneurysm sac. The clip 500 and delivery wire 512 fits within the lumen of the catheter 514.

Referring to FIGS. 13A-13D, the delivery wire 512 is releasably connected to the proximal surface of the connecting joint 506. As discussed above, the various suitable means known to those skilled in the art include mechanical, chemical, electrolytic, temperature-sensitive, remotely-triggered, or other type of release means. In one embodiment, the delivery wire 512 is oriented substantially perpendicularly to the horizontal axis of the self-expanding members 502 and 504. Alternatively, it can be oriented in variable angulated fashion relative to the horizontal axis of the self-expanding members 502 and 504. The delivery wire 512 allows for various movements of the self-expanding members 502 and 504 in relation to the catheter 514 or in relation to the neck of the aneurysm. In one embodiment, when affixed, the delivery wire 512 can facilitate minor changes in the position of the self-expanding members 502 and 504 during use. Also, the delivery wire 512 can also increase positional stability of the self-expanding members 502 and 504.

Figure 15:
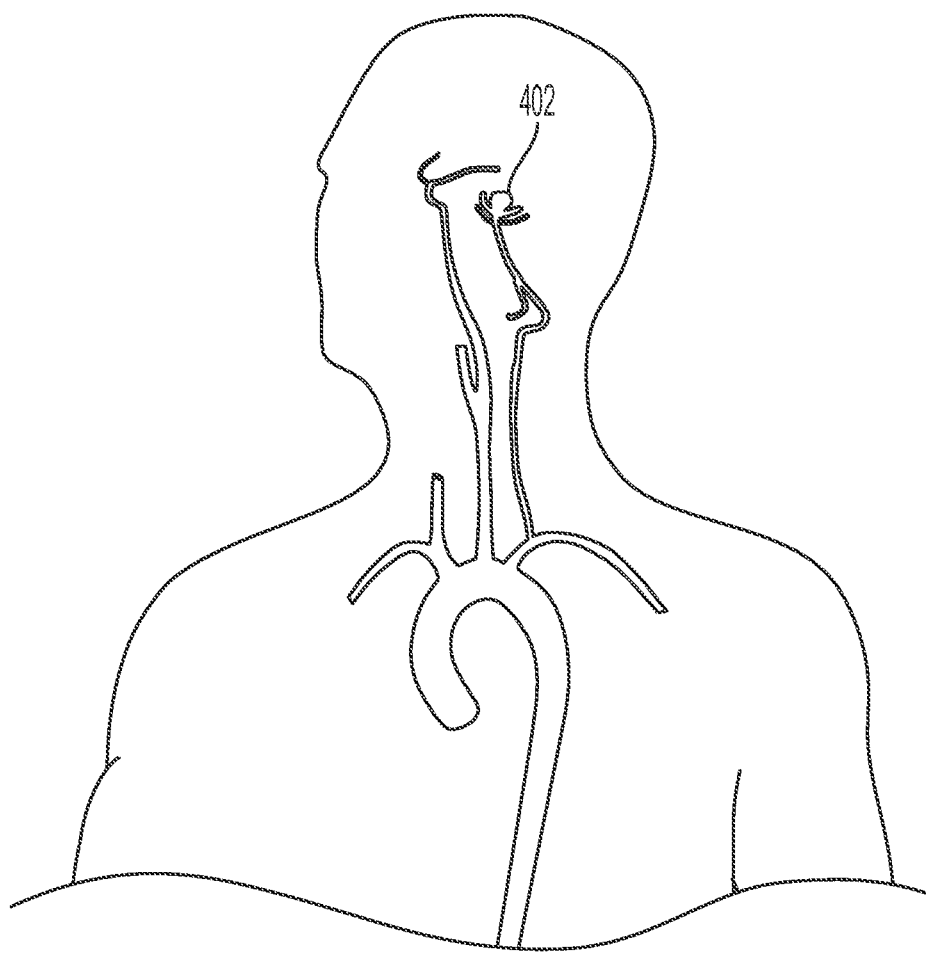
FIG. 15 illustrates a patient with a brain aneurysm to be treated with one embodiment of the present disclosure.

According to another aspect of the present disclosure, there is a method of treating an aneurysm, particularly a brain aneurysm 402 of FIG. 15, using the endovascular clips of the present disclosure, such as clip 500 or clip 600. While the disclosure may refer to numerical components of clip 500, it is understood that the discussion is applicable to clip 600 and its components. In one embodiment, an angiographic evaluation of the aneurysm is performed. Based on the anatomical data obtained, namely the measurements of the aneurysm neck dimensions in several planes, the shape and configuration of the aneurysm neck, the shape and branching pattern of the parent vessels, and the angle of attachment of the aneurysm to the parent vessels, a suitable clip 500 is selected. Referring to FIG. 13, in one embodiment, the anatomical data provides the shape of the circumference of self-expanding members 502 and 504, as well as the diameter, three-dimensional properties (e.g., concave, convex, flat), thickness, etc.

For instance, referring to FIG. 15, aneurysm 402 is generally known as a bifurcation aneurysm, which is often difficult to treat with conventional means, such as coils and stents, due to the "T" configuration of the main artery. For this type of aneurysm, a clip 500 with concave self-expanding members 502 and 504 may be the most appropriate. On the other hand, for a side wall aneurysm, a clip 500 with flat self-expanding members 502 and 504 may be more appropriate. Also, an aneurysm that is relatively smaller may benefit from a clip with only one lattice, such as clip 600. While FIG. 15 shows a bifurcation aneurysm in the brain, the embodiments of the present disclosure are applicable to other types of aneurysm occurring elsewhere in the body.

Referring to FIG. 16, in one embodiment, the size of the self-expanding members 502 and 504 of clip 500 is slightly larger than the neck 404 of the aneurysm 402. Preferably, the diameter of the self-expanding members 502 and 504 is about 0.5 to 3 mm larger than the diameter of the neck, and more preferably about 1-2 mm larger. The slightly larger size allows the clip 500 to substantially or completely cover the neck of the aneurysm when the self-expanding members 502 and 504 are fully deployed proximally and distally.

Figure 16A:
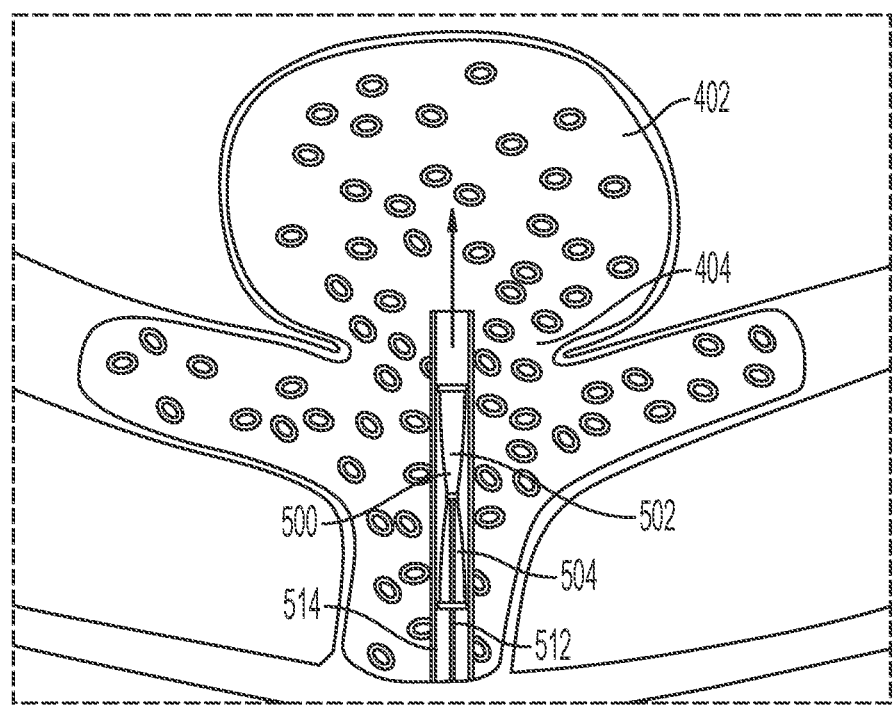
FIG. 16A is a side view of the preferred embodiment of the present disclosure in a collapsed state being inserted into the aneurysm of FIG. 15.
Figure 16B:
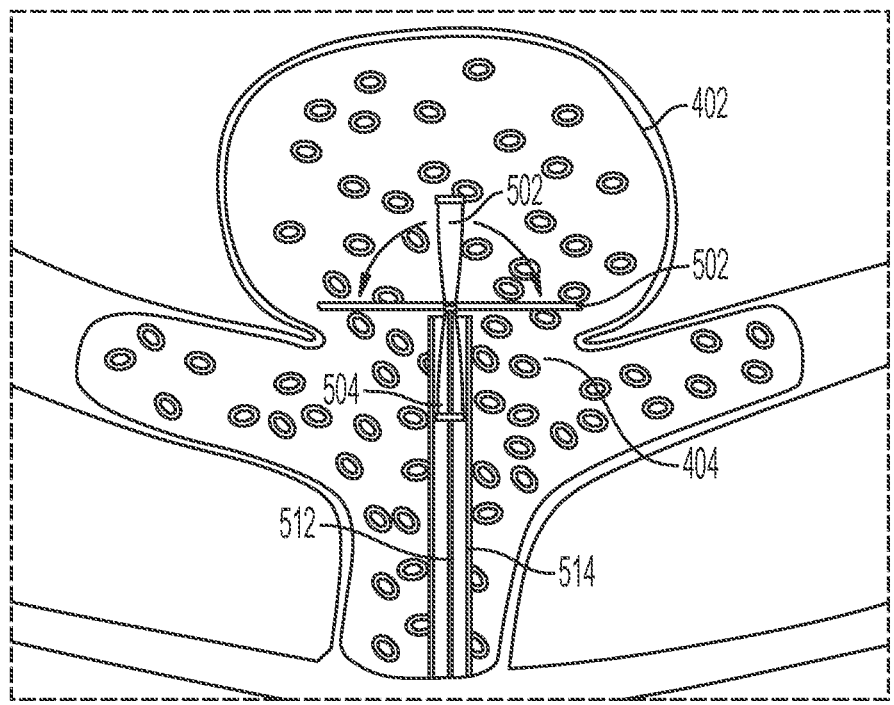
FIG. 16B is a side view of the preferred embodiment of the present disclosure partially deployed from a catheter into a non-collapsed state within the aneurysm of FIG. 15.

In one embodiment, under life fluoroscopic imaging the delivery catheter is advanced over a wire to a position just inside the aneurysm sac. Referring to FIG. 16A, the selected clip 500 is loaded inside the proximal end of the catheter, where the clip 500 is longitudinally folded and constrained in the collapsed condition inside the lumen of catheter 514. Referring to FIGS. 16A and 16B, using a detachable delivery wire 512, the clip 500 is pushed distally through the catheter lumen until the distal self-expanding member 502 is pushed beyond the distal end of the catheter 514 and into aneurysm 402. At this point, the expanding member 502 is fully released from the catheter 512 and expanded within the interior of the aneurysm 402 to its biased shape. In embodiments having some superelastic material such as nitinol, the expansion is partially due to exposure to an activation mechanism such as temperature beyond the threshold temperature.

Figure 16C:
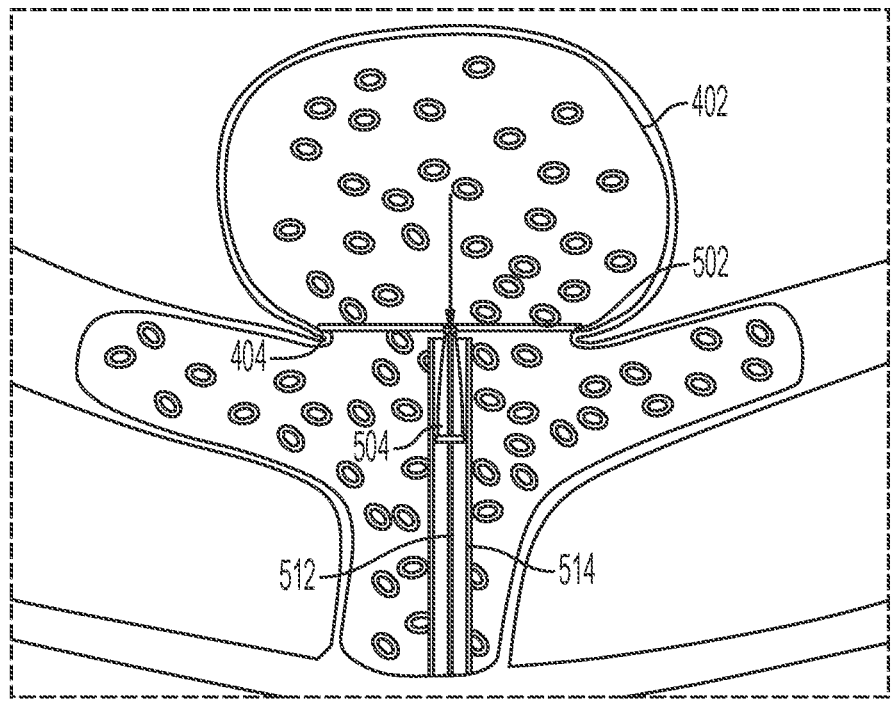
FIG. 16C is a side view of the preferred embodiment of the present disclosure in a non-collapsed state at the neck of the aneurysm of FIG. 15.
Figure 16D:
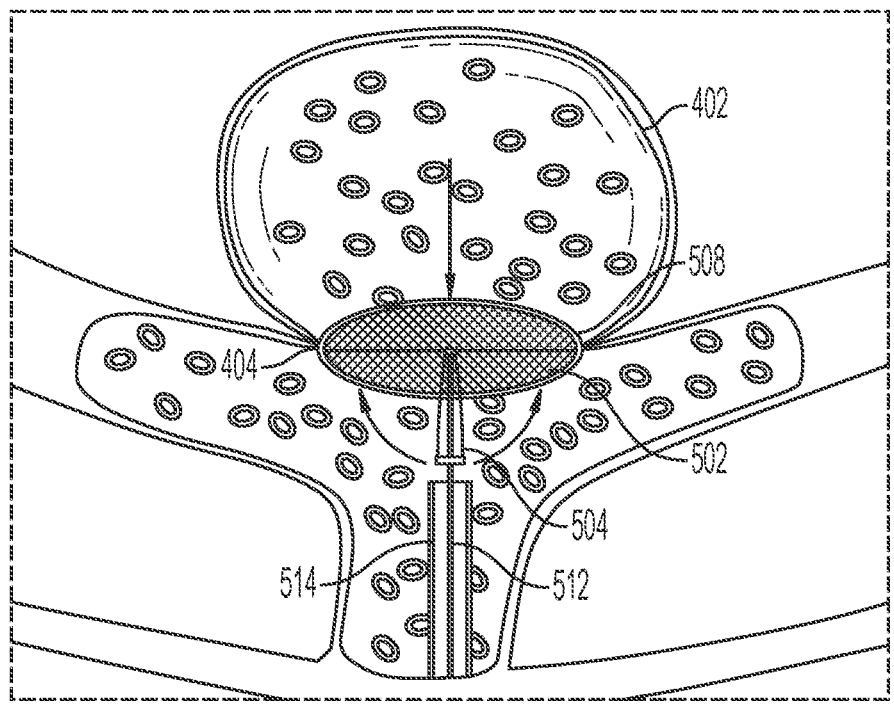
FIG. 16D is a perspective view of the preferred embodiment of the present disclosure in a non-collapsed state at the neck of the aneurysm of FIG. 15.
Figure 16E:
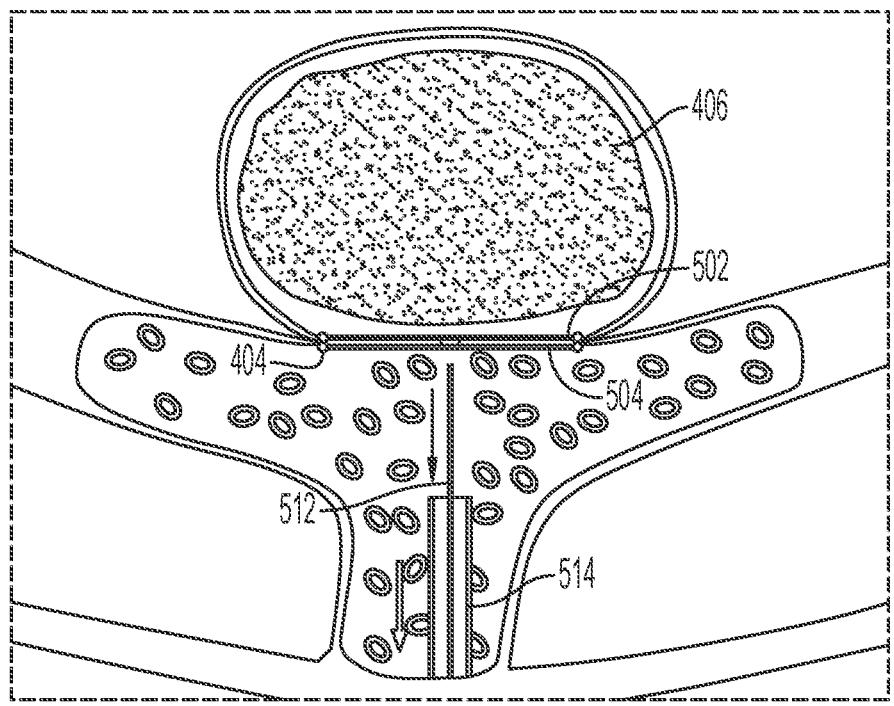
FIG. 16E is a side view of the delivery wire detaching from the preferred embodiment of the present disclosure completely deployed in a non-collapsed state.
Figure 16F:
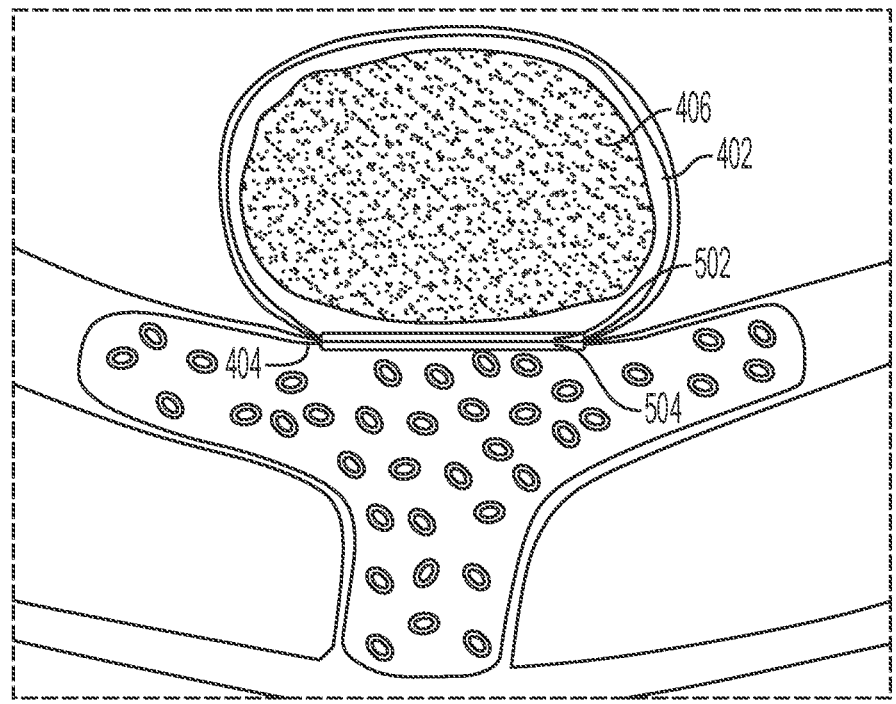
FIG. 16F is a side view of the aneurysm of FIG. 15 treated with the preferred embodiment of the present disclosure.

In one embodiment, referring to FIG. 16C, the distal member 502 is then pulled toward the neck 404 so that it touches the inside walls of the aneurysm neck 404. While stabilizing the distal member 502 in position by holding the delivery wire 512 in place, the catheter 514 may be slowly retracted to uncover the proximal self-expanding member 104 outside the aneurysm neck. Referring to FIG. 16D, at this point, the proximal self-expanding member 504 is fully released from the catheter 514 and deploys to its biased shape. Referring to FIGS. 16D-16F, the self-expanding member 504 also moves toward the distal self-expanding member 502, thereby clinching the neck 404 of the aneurysm between the two members 102 and 504.

In one embodiment, referring to FIG. 12, the framed wire segments or mesh of the self-expanding members 502 and 504 are inter positioned so that the spaces between the wires are substantially blocked. Referring to FIGS. 16E and 16F, after the self-expanding members 502 and 504 are fully deployed and positioned at the neck 404 of aneurysm 402, the delivery wire 512 is detached from the joint 506 and removed from the body of the patient. Once attached, the clip 500 impede further flow into the aneurysm from the artery by the density and arrangement of the mesh of the self-expanding members 502 and 504 where the openings of one mesh is covered with the strands of another mesh. The obstruction of the interstices can be further supported by the configuration of the self-expanding members 502 and 504 slightly pressing against one another. In embodiments using clip 600 of FIG. 14, the lattice of one self-expanding member is sufficient to serve as the barrier.

Referring to FIGS. 12C, 14, 16E, and 16F, in embodiments where the mesh of at least one self-expanding member, preferably distal member 502, is coated with a swellable material, the swellable material reacts either at the presence of fluid and/or higher temperature and swells up to seal any remaining opening of the self-expanding members 502 and 504. In one embodiment, the swellable material and arrangement of the mesh of the self-expanding members 502 and 504 completely seals the neck of the aneurysm and block the blood flow into the aneurysm with the resultant aneurysm thrombosis, i.e., formation of clot 406, and occlusion of the aneurysm. The swellable material may be activated by an external stimuli instead of or in addition to being exposed to a fluid and/or higher temperature. One example of an external stimuli is applying an electrical current to the endovascular clip 500.

In another embodiment, the mesh of at least one expanding member, preferably the distal self-expanding member 504, is further coated the bioactive material or eluting drugs as described above. In these embodiments, the bioactive material or eluting drugs can further accelerate occlusion and healing of the aneurysm by inducing thrombosis and scar formation as well as stimulation of the lining of the vessel to grow on and cover the disc with disc acting as a scaffolding upon which the cells grow which also lead to complete sealing the neck of the aneurysm and block the blood flow into the aneurysm with the resultant aneurysm thrombosis i.e., formation of clot 406, and closure. The healing of the aneurysm is achieved at least by the bioactive material or eluting drugs stimulating the healing of the lining of the blood vessel, which leads to encapsulation of the aneurysm.

The claims are not to be interpreted as including means-plus- or step-plus-function limitations, unless such a limitation is explicitly recited in a given claim using the phrase(s) "means for" or "step for," respectively.

Although the present disclosure and certain of its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method for treating an aneurysm in a patient by occluding the aneurysm with an endovascular clip, said method comprising the steps of:
    extending a distal self-expanding member of the endovascular clip within an aneurysm across the opening of an aneurysm neck, wherein the distal self-expanding member comprises a mesh of intersecting and interposed wires comprising openings among the intersecting and interposed wires;
    extending a proximal self-expanding member of the endovascular clip across the opening of the aneurysm neck, wherein the proximal self-expanding member comprises one or more radially-configured support wires;
    wherein a portion of the proximal and distal self-expanding members are each attached to a joint component through a wire and;
    wherein each of the proximal and distal self-expanding members comprise a self-expanding material configured to have an original configuration and a deformed configuration;
    wherein upon deployment at the aneurysm the proximal and distal self-expanding members extend across opposite sides of the aneurysm neck in the original configurations;
    wherein extending the proximal self-expanding member at the aneurysm opening occurs by moving the proximal member along a wire to position the proximal self-expanding member opposite the distal self-expanding member to clinch the aneurysm neck between the proximal and distal self-expanding members,
    wherein upon the clinching, the cross-section of the distal self-expanding member and the proximal self-expanding member are generally parallel to one another.

2. The method of claim 1, wherein the proximal and distal self-expanding members anchor the endovascular clip across the neck of the aneurysm.

3. The method of claim 1 further comprising the step of:
    delivering a swellable material configured to expand in volume upon exposure to an activating condition to the aneurysm by coating a portion of at least one of the proximal and distal self-expanding members with said swellable material.

4. The method of claim 3 wherein said swellable material fills openings in the distal self-expanding member mesh wires.

5. The method of claim 3, wherein the swellable material forms a barrier that prevents blood flow into the aneurysm.

6. The method of claim 3 wherein the swellable material is selected from the group consisting of hydrogel, hydrogel foam, hydrophilic polymers with conjugated collagen, hydrophilic polymers without conjugated collagen, porous hydrated polyvinyl alcohol foam (PAP) gel, and any combination thereof.

7. The method of claim 1 further comprising the step of:
    delivering a bioactive material configured to promote cell growth to said aneurysm by coating a portion of at least one of the proximal and distal self-expanding members with said bioactive material.

8. The method of claim 7, wherein the bioactive material comprises a thrombogenic material selected from the group consisting of collagen, fibrinogen, vitronectin, other plasma proteins, growth factors, peptides of said growth factors having attached RGD (arginine glycine-aspartic acid) residues, phospholipids, polymers with phosphorylcholine functionality, and any combination thereof.

9. The method of claim 1, further comprising delivering the endovascular clip through a vessel in a catheter.

10. The method of claim 9, wherein the proximal and distal self-expanding members are longitudinally folded and constrained in deformed configurations in the catheter.

11. The method of claim 9, further comprising deploying the endovascular clip from the catheter and guiding the endovascular clip to the aneurysm with a delivery wire.

12. The method of claim 11, wherein the joint component is located on the delivery wire.

13. The method of claim 11, further comprising disengaging the joint component to separate the delivery wire from the endovascular clip.

14. The method of claim 13, wherein disengaging comprises employing a release mechanism selected from the group consisting of mechanical, chemical, electrolytic, temperature-sensitive, and remote-triggered release mechanisms.

15. The method of claim 11, wherein guiding the endovascular clip to the aneurysm comprises visualizing a radiopaque portion of the endovascular clip.

16. The method of claim 15, wherein the radiopaque portion is present on at least one of the connecting joint and at least one of the expandable members.

17. The method of claim 15, wherein the radiopaque portion comprises platinum, tantalum, or nitinol.

18. The method of claim 1, wherein the distal self-expanding member further comprises a reinforcing wire having a diameter larger than a mesh wire diameter.

19. The method of claim 1, wherein the distal self-expanding member further comprises a peripheral frame.

20. The method of claim 1, wherein an extended distal self-expanding member mesh is a two-dimensional mesh.

21. The method of claim 1, wherein the self-expanding material changes from deformed configuration to original configuration at least by exposure to an activating condition.

22. The method of claim 21, wherein the activating condition is a temperature above a threshold temperature.

23. The method of claim 1, wherein the distal self-expanding member and the proximal self-expanding member act as scaffolds on and around which vasculature cells grow.

* * * * *